United States Patent [19]

Erikson et al.

[11] Patent Number: 5,301,674
[45] Date of Patent: Apr. 12, 1994

[54] METHOD AND APPARATUS FOR FOCUSING TRANSMISSION AND RECEPTION OF ULTRASONIC BEAMS

[75] Inventors: Kenneth R. Erikson; Syed O. Ishrak, both of Los Gatos; Wilbur A. Reckwerdt, Campbell; Ray S. Spratt, San Jose, all of Calif.

[73] Assignee: Diasonics, Inc., Milpitas, Calif.

[21] Appl. No.: 859,069

[22] Filed: Mar. 27, 1992

[51] Int. Cl.⁵ .................... A61B 8/00; G01N 29/00
[52] U.S. Cl. .................... 128/661.01; 73/625
[58] Field of Search ............ 128/660.09, 660.07, 128/661.01; 73/625–676

[56] References Cited

U.S. PATENT DOCUMENTS

| | | | |
|---|---|---|---|
| Re. 31,362 | 8/1983 | Shenk | 352/140 |
| 3,898,840 | 8/1975 | McElroy | 73/626 |
| 4,117,446 | 9/1978 | Alais | 73/606 |
| 4,137,777 | 2/1979 | Haverl et al. | 73/620 |
| 4,154,113 | 5/1979 | Engeler | 73/626 |
| 4,207,772 | 6/1980 | Stoller | 73/620 |
| 4,208,916 | 6/1980 | Thomenius et al. | 128/660.07 |
| 4,218,768 | 8/1980 | Hassler | 73/612 |
| 4,235,111 | 11/1980 | Hassler | 73/626 |
| 4,242,911 | 1/1981 | Martin | 73/626 X |
| 4,258,574 | 3/1981 | Hildebrand et al. | 73/625 |
| 4,275,597 | 6/1981 | Quedens et al. | 73/618 |
| 4,305,296 | 12/1981 | Green et al. | 73/626 |
| 4,307,613 | 12/1981 | Fox | 73/626 |
| 4,328,707 | 5/1982 | Clement et al. | 73/618 |
| 4,332,171 | 1/1982 | Iida et al. | 73/626 |
| 4,383,447 | 5/1983 | Kretz | 73/626 |
| 4,387,597 | 6/1983 | Brandestini | 73/626 |
| 4,395,912 | 8/1983 | Hassler | 73/626 |
| 4,398,539 | 8/1983 | Proudian | 73/626 |
| 4,409,982 | 10/1983 | Plesset et al. | 73/626 |
| 4,437,348 | 3/1984 | Sasahi et al. | 73/625 |
| 4,442,713 | 4/1984 | Wilson et al. | 73/599 |
| 4,442,715 | 4/1984 | Brisken et al. | 73/626 |
| 4,459,853 | 7/1984 | Miwa et al. | 73/626 |
| 4,487,073 | 12/1984 | Sumino | 73/626 |
| 4,516,583 | 5/1985 | Richard | 73/626 |
| 4,532,933 | 8/1985 | Hokanson | 73/642 |
| 4,534,221 | 8/1985 | Fife et al. | 73/626 |
| 4,537,074 | 8/1985 | Dietz | 73/625 |
| 4,569,231 | 2/1986 | Carnes et al. | 73/626 |
| 4,582,065 | 4/1986 | Adams | 73/626 |
| 4,608,868 | 9/1986 | Green | 73/606 |
| 4,629,927 | 12/1986 | Samodovitz | 310/334 |
| 4,665,924 | 5/1987 | Saito et al. | 73/631 |
| 4,677,981 | 7/1987 | Coursant | 73/628 |
| 4,730,495 | 3/1988 | Green | 73/620 |
| 4,784,147 | 11/1988 | Moshfeghi | 128/653 |
| 4,813,279 | 3/1989 | Shirasaka | 73/626 |
| 4,815,043 | 3/1989 | Shirasaka | 73/625 X |
| 4,819,652 | 4/1989 | Micco | 128/661.09 |
| 4,823,773 | 4/1989 | Naser et al. | 128/24 AA |
| 4,852,577 | 8/1989 | Smith et al. | 128/660.07 |
| 4,862,892 | 9/1989 | Green | 128/660.07 |
| 4,865,042 | 9/1989 | Umemura et al. | 128/660.03 |
| 4,870,971 | 10/1989 | Russell et al. | 128/661.01 |
| 4,974,211 | 11/1990 | Corl | 73/626 |
| 5,024,094 | 6/1991 | Kubota et al. | 73/634 |
| 5,033,456 | 7/1991 | Pell et al. | 128/24 EL |
| 5,060,652 | 10/1991 | Umemura et al. | 128/661.01 |
| 5,065,763 | 11/1991 | Green et al. | 128/660.07 |
| 5,072,735 | 12/1991 | Okazaki et al. | 73/625 X |
| 5,143,075 | 9/1992 | Ishizuka | 128/661.01 |
| 5,144,954 | 9/1992 | Satake et al. | 128/661.01 X |

OTHER PUBLICATIONS

Webb, Robert H., entitled "Confocal Microscopes", *Optics & Photonics News*, Jul. 1991, pp. 7–14.

*Primary Examiner*—Francis Jaworski
*Attorney, Agent, or Firm*—Blakely, Sokoloff, Taylor & Zafman

[57] ABSTRACT

An ultrasound imaging system for performing dynamic focusing of ultrasonic waves during transmit and receive. The present invention includes a method and a means for transmitting ultrasonic waves to a multiple depths within a body. The present invention optimizes the transmit frequency for each of the multiple depths to localize the energy of the ultrasonic waves. The present invention also includes a method and means for performing dynamic receive focusing of the reflected ultrasonic waves produced by discontinuities in the body, such that it is focused to receive ultrasonic waves from the depth at which the transmitted ultrasonic waves are focused.

39 Claims, 5 Drawing Sheets

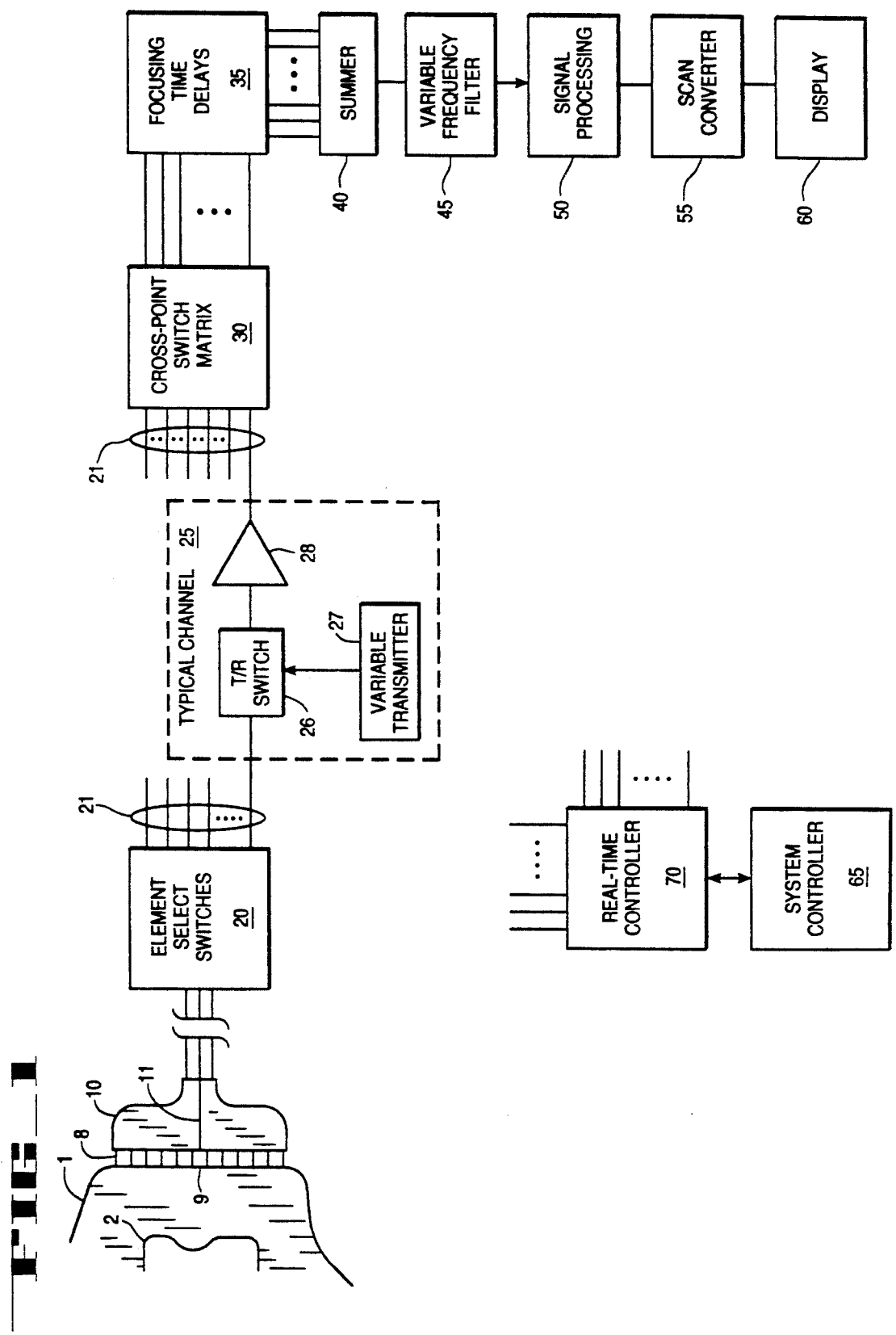

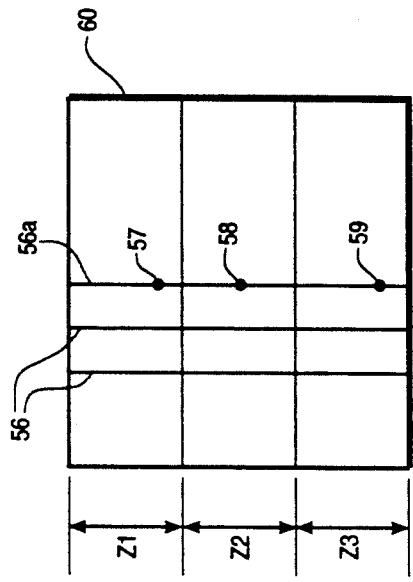
FIG._2A
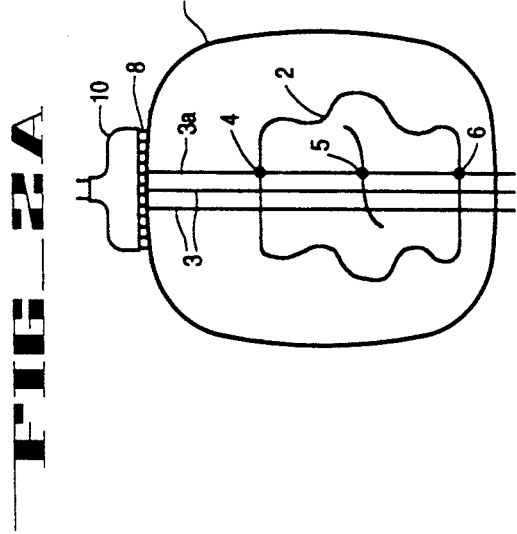
FIG._2B
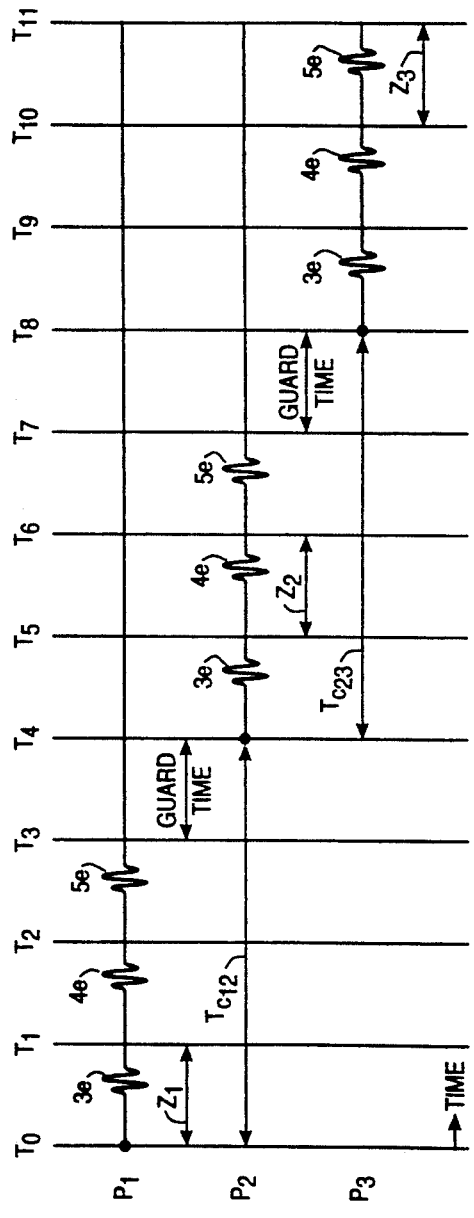
FIG._2C (Prior Art)

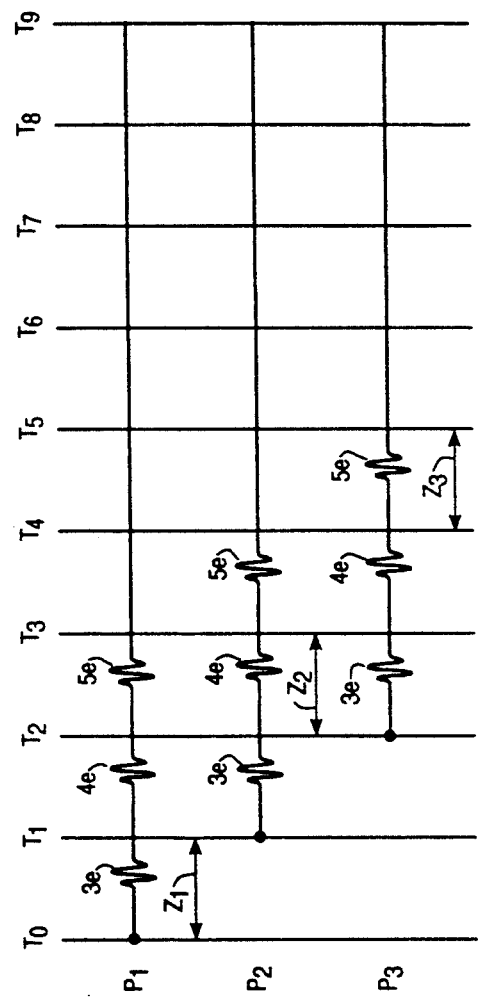
FIG._2D
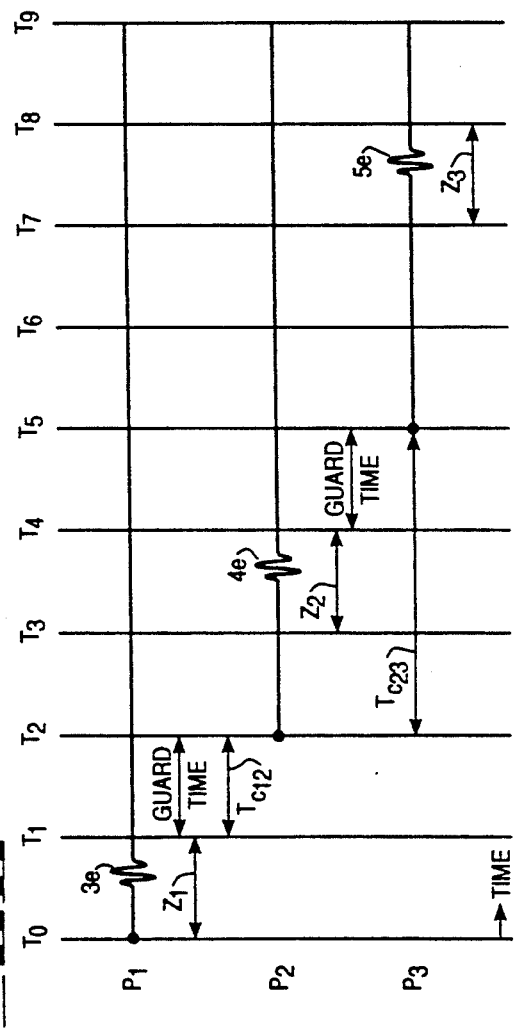
FIG._2E

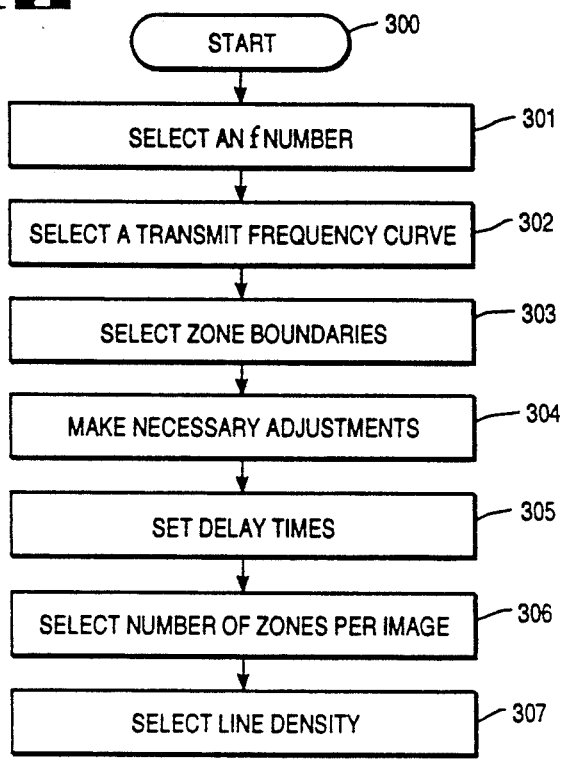
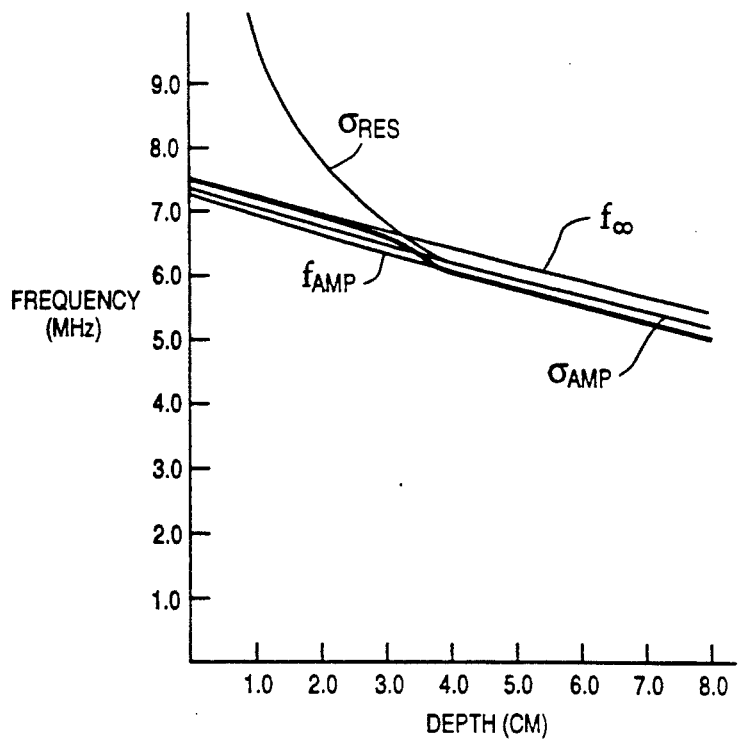
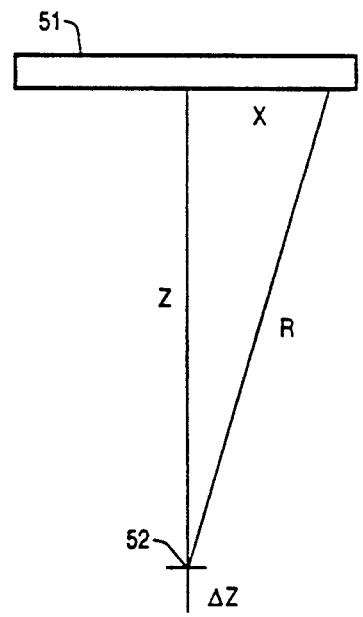

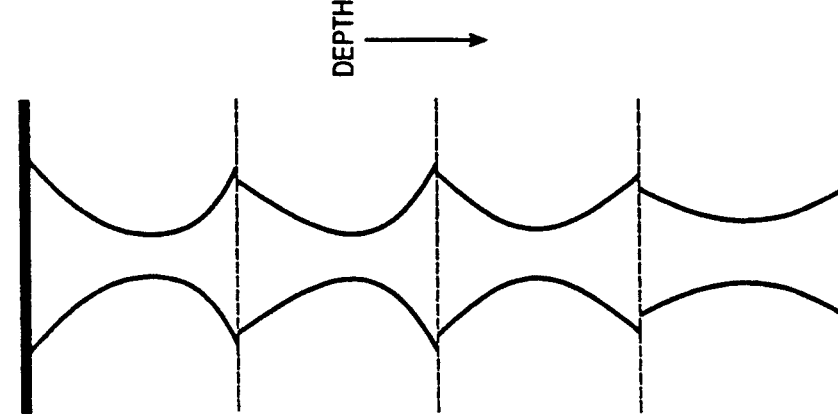
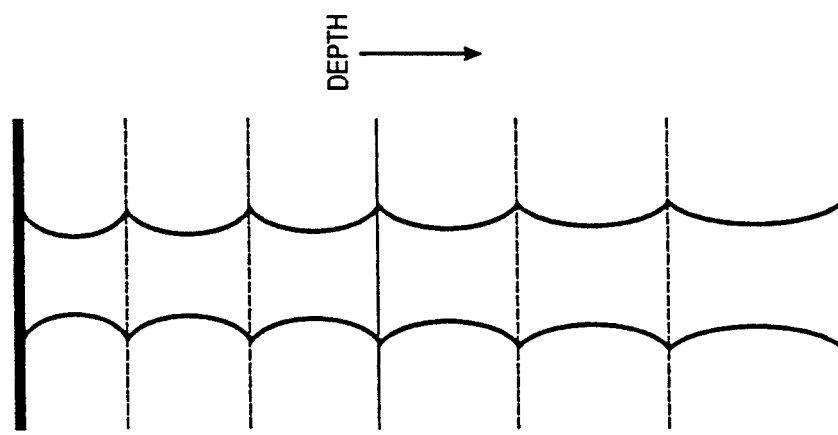
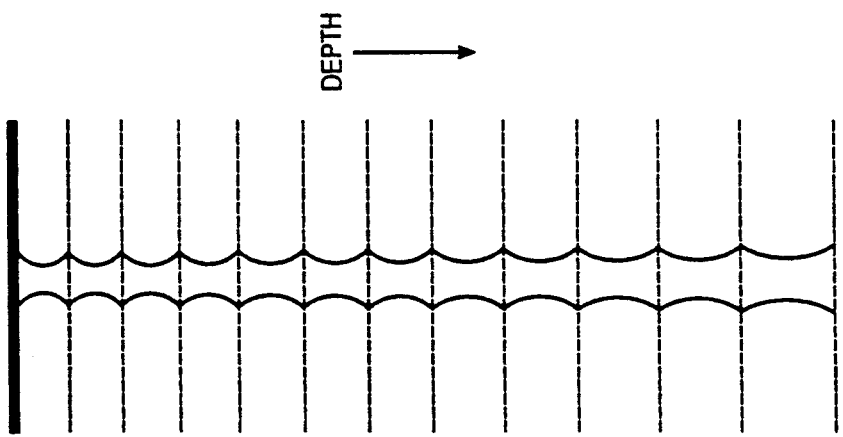

METHOD AND APPARATUS FOR FOCUSING TRANSMISSION AND RECEPTION OF ULTRASONIC BEAMS

FIELD OF THE INVENTION

The present invention relates to the field of ultrasonic imaging; in particular, the present invention relates to an apparatus and method for focusing an ultrasonic beam during transmission and reception.

BACKGROUND OF THE INVENTION

Pulse-echo ultrasonic imaging technology has become a vital tool for clinicians for examining the internal structure of living organisms. In the diagnosis of various medical conditions, it is often useful to examine soft tissues within the body to show structural details of organs and blood flow in these organs. Experienced clinicians can use this information in diagnosing various pathologies.

To examine internal body structures, ultrasonic images are formed by producing very short pulses of ultrasound using a transducer, sending the pulses through the body, and measuring the properties of the echoes (e.g., amplitude and phase) from targets at varying depths within the body. Typically, the ultrasound beam is focused at various depths within the body in order to improve resolution or image quality. The echoes are received by a transducer, typically the same transducer used for transmission, and processed to generate an image of the object, usually referred to as a B-scan image.

The transducers used in ultrasonic imaging are typically multiple element arrays in which electronic processing is used to focus the ultrasonic beam to improve lateral resolution. To focus the beam, the acoustic energy radiating from the transducer is concentrated or aimed at a single point, called the focal point. The ultrasound waves launched by each element of the array are time delayed with respect to each other, such that the waves from each element add up constructively at the focal point, creating a large acoustic intensity. In earlier ultrasound imaging systems which used a single element transducer, this focusing was usually performed by an acoustic lens or by curving the element itself. The focusing method used in an array, thus, simulates the focusing of the lens.

Upon reception of the ultrasound echoes from the body, each element is connected to a receiving circuit containing time delay circuits which are used to focus the transducer during reception. After each transmission pulse, the transducer waits for the receiving circuit to receive the echoes from the furthest depths before it sends out another transmission pulse.

For multi-element array transducers, if the same element time delays are utilized in transmission and reception, then the transmission and reception beam patterns will be identical. However, differences exist between transmit and receive focus. To focus ultrasonic waves on transmit, the time delays are fixed, such that the beam focal parameters are irreversibly set for that particular transmission pulse. Therefore, with transmit focusing, the focus cannot be changed, once the pulse has been launched.

On reception, however, the time delays can be changed continually and rapidly so as to follow the pulse as it propagates into the body at the speed of sound, thus forming a time-varying and focused received beam pattern. Thus, the received ultrasound beam can be kept in focus over a wide range of depths. By shifting the receiver focus in this manner, the best spatial resolution and image quality is obtained.

Since the transmitted beam can only be focused from pulse to pulse, it is common to create an image focused at a specific and operator selectable depth. This is called single zone focusing.

An extension of single zone focusing uses multiple sets of focused transmitted beams to create a composite image. Each set is focused at a specific depth. This is usually called multiple zone focusing. Generally, the number of zones varies from three to five zones. In this manner, real-time images are obtained with improved focus in certain regions in the image. This increase in image quality usually results in lower frame rates. Lower frame rates mean that moving structures or blood flow are not easily imaged and diagnosis may be impaired.

Frame rate reduction typically occurs with multi-zone focusing because each transmit zone requires almost the same acquisition time as a single zone, even though only a portion of the received data is used in the final display. The reason for this seemingly excessive time is because significant received signals continue to be received from regions in the image beyond the focal depth. Thus, a new transmit pulse for focusing at a zone cannot be sent until the entire line has been received. Otherwise, data from one zone would interfere with the data from another zone. The time delays between transmission of the separate pulses for an entire line of the image are referred to as the critical time delays. In practice, due to low frames rates, only a few zones are ever used.

The prior art has attempted to alleviate this disadvantage of low frame rates by such expedients as increasing the intensity of pulses transmitted to deeper zones compared to pulses transmitted to nearer zones, but such techniques have not resulted in any significant improvement in frame rates or in the number of zones available at a given frame rate, as a practical matter.

As will be seen, the present invention provides methods for increasing the number of zones without decreasing the frame rate together with a comprehensive method for optimizing these parameters. These methods permit a large number of zones to be used in practice. In effect, this results in simultaneous transmit and receive focusing at all depths in the image.

SUMMARY OF THE INVENTION

It is an object of the present invention to obtain uniform resolution in an ultrasonic image by "continuously" focusing the ultrasound beam while transmitting and receiving ultrasonic pulses.

It is an object of the present invention to concentrate the transmitted energy of the ultrasonic pulses and to localize detection of the reflected echoes from within an object in order to provide high frame rate ultrasonic images.

It is also an object of the present invention to localize the energy of the transmitted ultrasonic pulses by varying the frequency of the transmitted ultrasonic waves.

It is another object of the present invention to localize the detection of energy through selectively utilizing different frequency components of the received signal through using a variable frequency filter.

It is a further object of this invention to utilize wide bandwidth matched impedance transducers to optimize the energy transfer into and out of the object being imaged and to provide a wider frequency capability for optimizing precision energy concentration.

It is yet another object of the present invention to localize the energy of the ultrasonic waves during transmit by varying the bandwidth of the pulse of the ultrasonic waves during transmit.

These and other objects of the present invention are provided by a method and means for performing dynamic focusing of ultrasonic waves during transmit and receive. The present invention includes a method and a means for transmitting ultrasonic waves to a multiple depths within a body. The present invention optimizes the transmit frequency for each of the multiple depths to localize the energy of the ultrasonic waves. The present invention also includes a method and means for performing dynamic receive focusing of the reflected ultrasonic waves produced by discontinuities in the body, such that it is focused to receive ultrasonic waves from the depth at which the transmitted ultrasonic waves are focused.

BRIEF DESCRIPTION OF THE DRAWINGS

The present invention will be understood more fully from the detailed description given below and from the accompanying drawings of the preferred embodiment of the invention, which, however, should not be taken to limit the invention to the specific embodiment but are for explanation and understanding only.

FIG. 1 is a block diagram of the linear array ultrasound imaging system of the present invention.

FIGS. 2A, 2B, 2C, 2D and 2E illustrate an object imaged by both the prior art ultrasound system and the ultrasound imaging system of the present invention and their corresponding temporal sequences for ultrasonic pulse transmission.

FIG. 3 illustrates the currently preferred embodiment of the confocal focusing method of the present invention.

FIG. 4 illustrates an example of a transmit frequency curve resulting from the currently preferred embodiment.

FIG. 5 illustrates the spatial relationship between the transducer beam front and focal point.

FIGS. 6A, 6B, and 6C illustrate a comparison between the beam patterns produced by the present invention and traditional multi-zone focusing.

DETAILED DESCRIPTION OF THE INVENTION

An ultrasonic imaging apparatus and method for examining the internal structure of an object is described. In the following description, numerous specific details are set forth such as specific ultrasonic wave propagation characteristics, etc., in order to provide a thorough understanding of the present invention. It will be obvious, however, to one skilled in the art that the present invention may be practiced without these specific details. In other instances, well-known ultrasonic wave propagation characteristics and ultrasound processing operations have not been described in detail to avoid unnecessarily obscuring the present invention.

OVERVIEW OF THE ULTRASONIC IMAGING SYSTEM

FIG. 1 depicts a block diagram of the ultrasonic imaging system of the present invention. Referring to FIG. 1, the ultrasonic imaging system includes an ultrasonic probe 10, comprised of a linear array 8 of typical transducer elements 9 for transmitting ultrasonic pulses to and receiving ultrasonic pulses from an object 1. Ultrasonic probe 10 is coupled to element select switches 20 by cable 15, such that electrical conductor 11 is coupled to element select switches 20. Element select switches 20 are coupled to cross point switch matrix 30 by multiple channels 21. A typical channel 25 is shown. Referring to typical channel 25, one of the outputs of switches 20 is coupled to transmit/receive (T/R) switch 26. T/R switch 26 is coupled to variable frequecy transmitter 27 and the input of receive amplifier 28. The output of amplifier 28 is coupled to one of the inputs to matrix 30. Cross point switch matrix 30 is also coupled to focusing time delays 35. Focusing time delays 35 are also coupled to summer 40.

Summer 40 is coupled to variable frequency filter 45. Variable frequency filter 45 is coupled to signal processing module 50, which in turn is coupled to scan converter 55. Scan converter 55 is coupled to display 60. A real time controller 70 is coupled to and in control of all aspects of the imaging system within a single frame of the image. Other aspects of the system are coupled to and under system control 65.

Typical transducer element 9 is coupled to element select switches 20 of the ultrasonic imaging system by electrical conductor 11 which is part of cable 15. Cable 15 is typically a coaxially shielded wire. Element select switches 20 may be used to selectively turn on or off transducer elements in array 8. When selected, element 9 is coupled to transmit/receive switch 26, via element select switches 20, which permits high voltage variable transmitter 27 to send a very short voltage pulse or pulses to element 9 under the timing control of real time controller 70. In this manner, ultrasonic pulses are introduced into object 1 by element 9 and other selected elements of array 8.

Controller 60 regulates the respective transmitting times of elements in array 8 with respect to each other in such a way as to create a focus at a selected depth in object 1.

Echoes from target 2, within object 1, are reflected back to array 8, and in particular element 9 of array 8, and represent information about object 1 which is desired in the image. Transducer element 9 and other selected elements of array 8 then convert the ultrasonic echoes into electrical signals which are passed through element select switches 20 and transmit/receive switch 26, which real time controller 70 has now connected to receiver amplifier 28.

Amplifier 28 passes the echo signals through crosspoint switch matrix 30 which is also under control of real time controller 70. Amplifier 28 amplifies the very small signals from element 9 to voltage levels greater than the noise levels of cross-point switch matrix 30. Switch matrix 30 allows signals from element 9 to pass through to focusing delay circuits 35 and allows various combinations of elements of array 8 to be connected together with appropriate time delays with respect to other groups of elements of array 8 for receive focusing. Summer 40 then adds signals from focusing time delay module 35 to produce a single ultrasonic signal focused at a given depth in object 1.

The signal from summer 40 is then passed through a variable frequency filter 45 which is also under the control of real time controller 70. The frequency components of the resulting summed ultrasonic signal are then further processed in signal processing module 50 and sent to scan converter 55 for spatial registration as part of the ultrasound image of object 1 which is then finally displayed for operator viewing on display 60. Display 60 is typically a video monitor.

Transducer 8 in the present invention is a wideband matched impedance transducer. One continuing problem in ultrasound imaging systems has been the efficient conversion of electrical energy to acoustic energy when the piezoelectric transducer material has a different acoustic impedance than the human body. The matched impedance transducer 8 greatly improves such energy transfer.

In addition, strong ultrasonic signals reflected from nearby targets are repeatedly reflected back from the transducer face to the body, thereby causing an annoying haze in the image unrelated to any anatomical structure. The matched impedance transducer 8 utilized by the present invention greatly reduces the acoustic reverberations within the transducer, as well as between the transducer face and the object 1.

Furthermore, the matched impedance transducer 8 of the present invention provides increased bandwidth. Typical bandwidths of the matched impedance transducers of the present invention are nearly twice as large as the bandwidths of conventional "wideband" transducers. The currently preferred embodiment of transducer 8 is a linear array (-based) transducer having many individual transducer elements 9 which are constructed from a composite piezoelectric material. Transducer 8 transmits into and receives ultrasonic pulses from an object 1, such as a human body, being focused in both transmission and reception according to the present invention.

Ultrasonic pulses are reflected from the targets, such as target 2, which might be a tumor and boundaries which might be a bladder wall or the diaphragm within object 1. These reflected echo signals are received by typical transducer element 9 and sent to element select switches 20. These element select switches 20 allow individual array elements to be turned on or off by real time controller 60, depending on the nature of the focusing and scanning being performed.

To receive the small voltage signals resulting from the received ultrasonic pulses, transmit/receive switch 26, also under control of real time controller 70, is used to electrically isolate the high gain receiver 28 from the large voltage pulse generated by variable transmitter 27. Without this switch 26, receiver 28 would be overloaded for a long time period after the transmitted signal, which would result in a loss of received echo signals close to the transducer. Receiver 28 amplifies the small signals from transducer array 8 so that they are substantially larger than any stray noise which might arise in cross-point switch matrix 30.

Cross-point matrix switch 30 allows various combinations of array elements to be connected together for subsequent processing in focusing time delay module 35. Time delay module 35 introduces appropriate time delays between the signals coming from elements of the array in order to provide focusing on receive. Time delay module 35 is also under the control of real time controller 60 which generally adjusts the various time delays rapidly and within a single line to provide a variable depth focus. This focus is changed very rapidly, often at the speed of sound, so that as the transmitted pulse propagates into the object, the reflected signals are kept in focus.

Summer 40 simply adds the delayed signals from the various elements of array 8 such that a single signal is obtained. In the case of a single focal point on transmit and at the same focal point on receive (i.e., static focusing), this signal is in principle identical to that which would be received from a single element transducer focused with an acoustic lens.

Variable frequency filter 45, under control of real time controller 70, allows certain frequency components of the signal to be selected and passed on to additional signal processing 50, scan converter 55 and finally to the operator viewable display 60. The variable frequency filter 45 has two primary functions. First, its center frequency is adjusted with depth to match the spectral components of the returning signals when object 1 is a human body. Such frequency dependent attenuation creates a progressive loss with depth of high frequency pulse components and is a particular characteristic of soft tissue which is generally different than other materials. In addition, variable frequency filter 45, when used in conjunction with with changes in transmitted frequencies generated by variable transmitter 27, improves the discrimination between zones in the image allowing improved energy concentration.

Signal processing module 50 performs such functions as demodulation, additional filtering, Doppler or other flow detection processing and other kinds of vector processing well-known to those skilled in the art.

Scan converter 55 is generally a large two dimensional digital memory typically composed of at least 512 by 512 eight bit memory locations, although it may be much larger than that. This memory serves as a storage means for the vector information from a single line of ultrasound echoes. The scan conversion process converts such a vector, which in general may be oriented in any straight line direction, into a so-called raster scanning format which is suitable for displv 60. Display 60 is a standard television or computer type monitor.

OVERVIEW OF THE PRESENT INVENTION

The present invention provides a method and means for focusing the beam at all depths within an object on transmit and receive of the ultrasonic pulses. In order to do this, the currently preferred embodiment of the present invention uses several parameters to concentrate the transmitted sound energy at a specific depth and to selectively receive reflected energy from the same depth.

By concentrating energy on transmission and selecting reflected energy on reception successive pulses can be designed for minimum interference with previous pulses. By preventing pulses from interfering with one another, more pulses can be sent and received in a given time period, allowing more focal zones to be used in a real-time image without slowing the imaging frame rate down. More focal zones also means better resolution and image quality. Thus, image quality is improved without sacrificing any real time properties.

To transmit pulses so that they focus at different depths successively or to change the focus on reception, the system must rapidly change the relevant parameters. The present invention uses high speed reconfiguration through a real time controller. During the creation of an image, many or all parameters are completely reprogrammed at much faster rates than previously used in other systems. With such rapid programmability and using the methods of the present invention, the time between successive transmit pulses may be made much shorter than before, such that more transmit bursts are available per image.

With precision energy concentration of transmit and selective energy reception, together with high speed reconfiguration, there is no need to wait for the entire line to be received before transmitting the next pulse. Instead, shortly after the data is received from a given depth or zone in the object, ultrasound can be transmitted again.

The present invention allows for transmit and receive focus over an extended field of view, while maintaining a clinically usable frame rate. An example of the benefits of localizing the focus on transmit according to the present invention is shown in FIGS. 2A through 2E. FIGS. 2A-2E depict an example of a three zone case for simplicity, however, it should be noted that the present invention is not limited to using only three zones. FIG. 2A depicts an object being imaged. Referring to FIG. 2A, probe 10 containing transducer array 8 is applied to object 1, usually a human body, to image an internal structure 2. Other aspects of the ultrasound system as described in FIG. 1 are omitted from FIG. 2A to avoid obscuring the figure. FIG. 2B depicts the B-scan display 60 of the ultrasound system. For simplicity, the ultrasound system is shown as a linear array which produces a series of parallel vertical lines of ultrasound data 56 on display 60.

In FIG. 2A, vertical lines 3 are drawn through object 1 and internal structure 2 to depict the successive scanning positions of the ultrasound system. Line 3a is drawn so that it intersects the boundary of structure two at points 4 and 6. Line 3a also intersect another internal structure at point 5. The ultrasound system faithfully displays echoes from points 4 and 6 as points 57 and 59 respectively, and point 5 as point 58 in FIG. 2B. Points 57, 58 and 59 appear in zones Z1, Z2 and Z3 respectively of the display. Each of zones Z1, Z2 and Z3 correspond to a distinct depth into the body. To complete the image of object 1 and its internal structure 2, the system repeats such vertical scanning lines rapidly to form an entire B-scan image in real time. It should be noted that there are no moving parts and that all scanning is performed electronically. Once again referring to FIG. 2B and specifically the vertical line 56a containing points 57, 58 and 59, it should be noted that each of these points are depicted to be in zones 1, 2 and 3 respectively.

FIG. 2C which is representative of prior art systems with multi-zone focusing, depicts several successive ultrasound pulses P1, P2 and P3, along line 3a (FIG. 2A) with resulting echo times displayed on a horizontal axis as $t_0-t_{11}$. Pulse P1 is transmitted at time $t_0$. Echoes 3e through 5e are received from points 3 through 5 (FIG. 2A) at time delays corresponding to the travel time of pulse P1 from transducer 10 to the respective point and back to transducer 10. In FIG. 2C, echo 3e appears between time $t_0$ to $t_1$, echo 4e between time $t_1$ and $t_2$ and echo 5e between time $t_2$ and $t_3$ for pulse P1. It should be noted that pulse P1 generates echoes 3e through 5e and this prior art ultrasound system, which focuses the transmitted pulse in zone Z1, only displays the information from zone 1 which in this case is echo 3e. Echoes 4e and 5e are not displayed for pulse P1.

After an additional time delay (from $t_3$ to $t_4$) which is commonly referred to as a guard time, pulse P2 is then sent at time $t_4$, with the transmit focus set to zone Z2 and echo 4e is displayed. Once again, echoes 3e, 4e and 5e all occur from pulse P2. As shown, echo 3e occurs between time $t_4$ and $t_5$, echo 4e appears between time $t_5$ and $t_6$, and echo 5e appears between time $t_6$ and $t_7$. Similarly, pulse P3 is sent at time $t_8$ after an additional guard time (from $t_7$ to $t_8$) and used to focus in zone 3 and echo 5e may be displayed. Once again, echoes 3e, 4e and 5e are also produced by pulse P3 between times $t_8$ and $t_9$, $t_9$ and $t_{10}$, and $t_{10}$ and $t_{11}$ respectively. Each segment of data from the the respective zones is spliced together in scan converter 55 to form a continuous image on display 60.

Note that for each pulse, echoes from all points along the line 3a return to the transducer array. Furthermore, note that there is a delay time between the end of zone 1, (i.e., $t_1$) and the time when P2 is generated, that is the time between $t_1$ and $t_4$ which is denoted $tc_{12}$ in FIG. 2C. Similarly, a delay time exists between the end of zone 2 (i.e., $t_6$) and the time when pulse P3 is generated (i.e., the time between time $t_7$ and $t_8$).

This time tc is defined as the "critical time". The critical time is the minimum time between pulses to avoid artifacts in the image. Note that the time interval tc varies between pulses in FIG. 2C and that there is the additional guard time (e.g., time $t_3-t_4$ and time $t_7-t_8$) to insure that there are no extraneous pulses. Furthermore, note that these critical times determine the maximum pulse rate and, for a constant ultrasound line density in the image, therefore, the maximum frame rate of the real time imaging system.

This problem of artifact, well known to those skilled in the art, is depicted in FIG. 2D where a person attempts to increase the frame rate by violating this minimum critical time constraint and has not included any guard time. In this naive approach, pulse P1 is sent at time $t_0$ and is the same as before, such that the same echoes 3e, 4e and 5e are provided at the same times as in FIG. 2C. Pulse P2 is sent immediately after the end of zone Z1 (i.e., at time $t_1$) in violation of the minimum critical time. In this case, pulse P2 is sent at time $t_1$ and produces echo 3e during time $t_1-t_2$, echo 4e during time $t_2-t_3$, and echo 5e during time $t_4-t_5$. Note that echoes 4e and 5e are still returning to the transducer while additional echoes from pulse P2 begin to return. Since the ultrasound circuitry only can process the echoes it receives, there is no way to distinguish the echoes. In particular, in zone 2, the system sees echoes 4e and 3e superimposed. If pulse P3 is sent too soon, it can be seen that an echo 3e may also be superimposed in the received signals from zone Z2, further confounding the image through artifact. Although this particularly simple example with only a few points is clearly a problem, when a complex structure is imaged this problem becomes insurmountable in the prior art.

The details of the present invention and how it improves the imaging capabilities of an ultrasound system are shown in FIG. 2E. Referring to FIG. 2E, pulse P1 is sent at time $t_0$ to focus in zone Z1 and does so between time $t_0$ and $t_1$. Pulse P2 is sent at time $t_2$ after a guard delay from time $t_1$ to $t_2$ and is sent to focus in zone Z2, which it does during time $t_3-t_4$. Pulse P3 is sent at time $t_5$ after a guard delay time from time $t_4$ to $t_5$ and after the focus of pulse P2 between time $t_3$ and $t_4$. Note that in the received echoes from pulse P1, only echo 3e (from $t_0-t_1$) from zone Z1 is present. Echoes 4e and 5e are not there to confound the image as in FIG. 2D. Similarly, in pulse P2, only echo 4e (during time $t_3$ to $t_4$) from zone Z2 is present. Likewise, in pulse P3, only echo 5e (during time $t_7$ to $t_8$) from zone Z2 is present.

Thus, provided there is a way to selectively choose echoes from a given zone and to suppress echoes from other zones, the critical time can be minimized and higher frame rates can be achieved. Methods for suppressing such echoes from other zones comprise an important aspect of invention disclosed herein. Furthermore, as will be obvious to those skilled in the art, the guard time may also be minimized leading to even further improvements in pulse rate and frame rate.

To reiterate, if the same three zones were obtained using prior art multi-zone techniques, pulse P2 could not be transmitted until all of the echoes due to pulse P1 had been received (i.e., time $t_4$). Likewise, pulse P3 could not be transmitted until all of the echoes due to pulse P2 had been received (i.e., time $t_8$). Thus, using prior art multi-zone techniques, the same three zone diagram would require eleven time periods (i.e., time $t_0-t_{11}$). Therefore, the present invention provides a significant time advantage over the prior art.

It will also be obvious to those skilled in the art that the number of zones that can be utilized is not limited to three as in the example shown in FIGS. 2A, B, C, D and E and that the number of zones can be greatly increased, further contributing to improved resolution without sacrificing frame rate. It will also be obvious to those skilled in the art that greatly increasing the number of zones also requires a system which can be rapidly reprogrammed from zone to zone. Thus, for a given frame rate, which is generally determined by the needs of the clinician to view a certain tissue which may be moving, there is a maximum number of zones which can be employed and, therefore, a certain limit to the system resolution and image quality which may achieved with this method. Yet this invention provides significantly more zones and correspondingly better resolution and image quality for a given frame rate than has been possible with prior art.

PRECISION ENERGY CONCENTRATION OF TRANSMITTED PULSES

By localizing the energy at specific depths within the object, the rate at which successive transmit pulses can be sent increases, thereby increasing the frame rate. In order to localize the acoustic energy to a specific region in the body, the present invention sets a variety of transmit parameters, namely:

1. Center Frequency
2. Bandwidth
3. Transmitter Voltage
4. F-number-One-Dimensional Array
5. Two-Dimensional Array
6. Zone Sequences
7. Spatially Separated Line Sequences.

1. CENTER FREQUENCY

Typical matched impedance probes are inherently wide bandwidth, with fractional bandwidth typically approaching 90 to 100 percent. This means that for a typical 7.5 MHz array transducer, significant energy can be transmitted into the body from 4 MHz to 10 MHz.

In the currently preferred embodiment, center frequency optimization of the transmitted pulse is accomplished by choosing the highest frequency that will penetrate to the zone of interest and using only approximately 50% fractional bandwidths, which is appropriate for imaging. In this manner, the ultrasound pulses are localized to the specific zone and experience maximum attenuation in the following zones, such that any reflected pulses from the following zones are greatly reduced in strength and do not interfere with the transmitted and received energy from the zone of interest.

2. BANDWIDTH

The center frequency and the bandwidth are interrelated since the center frequency and bandwidth of the transmitted pulse are typically set by specifying the pulse width, duty cycle, and number of pulses sent by the transmitter. By optimizing the transmit frequency and bandwidth, the energy can be localized to a specific region. In the currently preferred embodiment, the energy can be varied by varying the number of pulses in the transmitted pulse with depth.

3. TRANSMITTER VOLTAGE

Although not currently used in the present embodiment, localizing the energy to a given zone can further be improved by minimizing the transmit pulse voltage to only that needed to reliably display the full range of echoes. This means that the transmit pulse voltage for each successive zone depth may be increased and to help overcome any returning interference from the previous, lower voltage zones.

4. F-NUMBER

The fourth transmit parameter is the f-number (i.e., aperture size vs. zone depth). As is well known in optics as well as acoustics, the f-number controls the depth of field or the length of the focal region. As the f-number increases, the depth of field increases. Similarly, if the f-number goes down, the depth of the field decreases. A low f-number indicates a large aperture to depth ratio and narrow depth of the field.

In the currently preferred embodiment, the f-number for transmitting to each of the zones is kept low and constant consistent with desired zone sizes and frame rates. By keeping the f-number low and constant, the ultrasound energy is focused more tightly. Keeping the f-number low and constant also helps eliminate interference from targets closer to the transducer because the beam is more spread out.

Maintaining a constant f-number also contributes to keeping the resolution of the image constant. When deep zones are being imaged, there may not be a large enough aperture available to maintain a constant f-number. Thus, maintaining a constant f-number is only possible for relatively near zones.

5. TWO-DIMENSIONAL ARRAYS

Although the above discussion of setting parameters to localize the energy of the ultrasonic pulses has only been discussed in conjunction with a one-dimensional array, it is also applicable to the case of a two-dimensional array composed of a rectangular or square matrix of individual transducer elements together with individual transmitter and receiver circuits as well as switching, focusing and summing circuits appropriate to the array. If such a two-dimensional array is used, the ultrasonic pulses can be focused in both dimensions (in the plane of the B-scan image as well as the plane perpendicular to the image), thereby also focusing the "out-of-plane" energy. By focusing in both directions, a better focus is obtained than in the one-dimensional array. This tighter focus allows even smaller zones to be used because the energy dies out quicker outside the focal region.

6. ZONE SEQUENCES

The sixth parameter to be optimized is the sequence of examining the zones. In the above discussion it has been assumed that each successive transmit pulse is focused to the next adjacent zone deeper in the body. In some circumstances, artifacts can be minimized by transmitting in a different order. For example, when imaging a full bladder, there is a large fluid filled region with very low acoustic attenuation closer to the transducer than deeper, more reflective tissue, such as the bladder wall. In this case, remnants of the reflections from the bladder wall from the first pulse can interfere with subsequent pulses. By transmitting a deep zone immediately before a less reflective zone, the artificats will be reduced, both because the reflectors beneath the deep zone are small and because the time between transmits is guaranteed to be long because of the long two-way travel time to the deep zone. Therefore, optimizing the sequence of zones for a specific application can often reduce artifacts. This may have a minor effect on frame rate, however, it is generally done in special cases to make the system more robust. Note that changing the order of transmission does not increase the frame rate.

7. SPATIALLY SEPARATED ZONES

Another parameter to be optimized in this invention is the sequence of lines in the image. An array ultrasonic imaging system can perform spatially separated line sequences by electronically selecting lines which are widely separated in space. This spatial separation helps ensure that the energy from a previous transmission pulse does not interfere with the current zone.

If the lines are widely separated, after transmitting the first line, the second line can transmitted immediately after the pulses from the bottom of the zone from the first line are received. This spatial line sequencing can also be combined with zone sequences as described above to produce maximum frame rates with minimum artifacts.

SELECTIVE ENERGY RECEPTION

In the currently preferred embodiment, there are two parameters to be optimized on reception:
1. Dynamic Receive Focusing and F-number-One Dimensional Array
2. Two-Dimensional Array
3. Dynamic Frequency Imaging.

1. Dynamic Receive Focusing and f-number-One Dimensional Array

Electronic focusing on reception is also a well known technique in ultrasound. It is the analog of focusing on transmission, i.e. to focus at the same point in either transmission or reception, the same relative time delays between elements of the array are required.

As in transmission focusing, use of a low f-number in reception improves the ability to selectively localize the region in the object from which echoes are received and to discriminate against other unwanted regions. Low f-numbers result in small focal spot diameter and reduced depth of focus which are both desirable.

2. Two Dimensional Array Receive Focusing

As described in the case of transmission, a two dimensional array may also be used to further improve the discrimination between desirable signals and those which are unwanted. By using the focusing properties in the plane perpendicular to the image plane in conjunction with conventional in-plane focusing, greatly improved performance may be obtained.

3. Dynamic Frequency Imaging

On reception, variable frequency filter 45, a bandpass filter whose center frequency may be rapidly adjusting, is used in conjunction with variable transmitter 27 to enhance the echoes from a given zone and to discriminate against those from other zones. The center frequency of filter 45 is adjusted to match the frequency of the ultrasound energy returning from the given zone (which was chosen according to preceding discussion of transmit optimization) The center frequency is also coordinated and controlled in conjunction with the parameters loaded from the tables which are discussed below. It should be noted that the dynamic frequency imaging utilized by the currently preferred embodiment of the present invention is only effective if the transducer is sufficiently wideband. Otherwise, the returning signals from all of the depths would have the same approximate frequency content and no depth dependent optimization would occur.

FINAL OPTIMIZATION—APPLICATION DEPENDANCE

Once the transmit parameters have been set (i.e., the number of zones have been determined) and the spot size selected, the critical delays between the ultrasonic pulses are determined from a computer model. These critical time delays are the time delays which result in an acceptable level of artifact and are generally dependent on each specific application.

The final critical time delays are then empirically determined for each set of transmit zones and each application. By being application dependent, the actual time delays (critical time delay plus guard time) vary for each type of application. For example, in a liver imaging application where the tissue is very deep and quite uniform and has little movement, the ultrasonic pulses attenuate rapidly and smoothly with little artifact. In this case, the actual empirical time delays may be as short as the critical time delays.

On the other hand, in applications where there fluids are involved, such as bladders and obstetrics, the ultrasonic pulses do not die off as quickly and deep bright reflectors are located beneath nearby echo free regions. In this case, additional guard times are required and the actual empirically determined time delays may be longer than the critical time delays.

In the currently preferred embodiment, for each zone N, the time delay until the next transmit is either the critical time delay or the critical time delay plus a guard time. The critical time delay $t_c$ is determined according to the equation below:

$$t_c = \frac{2Z_b(n)}{c} \tag{1}$$

where $Z_b(n)$=depth to the bottom of the nth zone and c is the speed of sound in tissue (which is assumed to be a constant). The transmit time delay is the greater of the critical time delays or the critical time plus the guard time, which is application dependent and must be empirically determined.

According to the present invention, each of these parameters are changed on a zone-by-zone basis in transmission, such that the energy from the ultrasonic wave is localized to the zone of interest and thereafter, attenuates quickly so that there is a minimum or acceptable level of artifact due to other pulses.

To reiterate, by setting the transmit parameters, the present invention allows the ultrasound imaging system to have a larger number of zones at a given frame rate, thus ensuring that the impulse response of the focusing system (i.e., the spot size) is subject to small, smooth variations with depth. By maintaining a relatively constant spot size, the focal quality of the image over an extended range of depth is consistent and substantially improved over the prior art.

SELECTION OF APPLICATION DEPENDENT PARAMETERS THROUGH ICONS

In the currently preferred embodiment, sets of transmit parameters, including transmit delays, are stored in the system control memory as tables which can be accessed by the operator. An example of one such table is shown in Appendix A. System controller (FIG. 1) has a operator interface which is typically displayed on display 60 and includes a set of icons, each corresponding to a set of tables in the currently preferred embodiment.

When an icon is selected, the disk storing the tables is accessed. In the currently preferred embodiment, the information includes transmit delays, the zone boundaries, the transmit frequencies, etc. for four confocal orders for that specific application. When an order is selected, the parameters in that table are loaded into the real time controller 60 and imaging can begin. In the currently preferred embodiment, the operator interface utilizes icons to represent a specific application. By selecting an icon, the operator immediately accesses a particular set of tables from the memory which represent the optimum set of parameter values consistent with the application.

In the currently preferred embodiment each icon has a choice of four application specific "orders" of confocal imaging: A, B, C and D. When selecting A, the user is selecting the table which has the poorest resolution but has the maximum frame rate and lowest level of artifacts. Orders B through D have progressively higher image quality, potentially higher levels of artifact, and lower frame rates. Each set of orders, and the parameter trade-offs among the orders, is different for each application.

The combination of methods for precision energy concentration and the flexibility of application dependent optimization provides for imaging capabilities that were not possible in previous systems. For example, a 3.5 Mhz probe may be used in several different applications ranging from looking for small stones in the bladder to detecting subtle tissue variations in the liver. For the bladder application, it is necessary to keep the bladder free from artifacts that might obscure the small stones.

For this icon order A would be set with very long critical times to ensure that no reverberation artifacts would appear. Order D would use shorter critical times, but might include half line scanning and more zones for situations where resolving a small lesion is required. Orders B and C would provide intermediate levels of trade-offs to ensure that a nearly optimal setting is available for all bladder applications.

The four orders available for the abdominal-liver icon are optimized based on different considerations. Order A requires some protection against artifacts, but substantially less than for the bladder. Since resolution is more important in this application, three simultaneous zones might be used even in the "low" resolution order. Order D would make full use of precision energy concentration by using a larger number of zones that were previously possible while maintaining usable frame rates. This high ultrahigh resolution mode would be used for diagnosing subtle texture variations. Again levels B and C would have intermediate values to provide smooth transition between Order A and Order D and to account for the range of patient and pathology differences expected in liver imaging applications.

Previous systems utilized only a few parameter selections to span all applications. Precision energy concentration thus permits a much greater range of optimization in imaging than was previously possible. Application dependent orders then allow for easy and logical adaptation to patient variables and pathological differences.

THE CURRENTLY PREFERRED EMBODIMENT OF THE CONFOCAL FOCUSING METHOD

The currently preferred embodiment for selecting the parameter used in the confocal focusing method of the present invention is shown in FIG. 3. Referring to FIG. 3, the transmit focusing method 300 comprises initially selecting an f-number (block 301). After an f-number has been selected, the transmit frequency curve is selected (block 302). Then the zone boundaries are selected (block 303). Once the zone boundaries have been selected, any necessary adjustments are performed (block 304). After adjustments, the delay times are set (block 305). Following the delay times, the number of zones per image is selected (block 306). Next, the line density is selected (block 307). Each of these steps are discussed below in order.

In actuality, the first step in optimizing the transmission parameters is the selection of a probe. Probes can be characterized by their center frequency $f_0$, their bandwidth $\sigma_0$ and their element dimensions. Once the probe has been selected, the transmit focusing method 300 may start.

SELECTION OF F-NUMBER

The f-number is the ratio between the distance from the face of the probe to the focus and the size of the aperture. As the f-number increases, the depth of field increases. Similarly, as the f-number decreases, the depth of field goes down. A low f-number indicates a large aperture, such that the depth of field is very small. Focusing ultrasonic waves in a small depth of field requires a "tighter" or stronger focus because the transmitted ultrasonic waves quickly become out of focus. In other words, a strong focus not only localizes the energy, but also causes the energy to diverge rapidly. By diverging rapidly, discontinuities and targets within the zone are not isonified with strong ultrasonic wave energy, thereby reducing the amount of reflection (i.e., echoes). Thus, when the reflected waves are not in focus, the spatial resolution in the zone diminishes. To ensure that the maximum amount of the zone is isonified with focused energy, the f-number is chosen so that small depths of field (i.e., tightly focused beams) have smaller transmit zones.

Since the f-number is related to the size of the zones, in the present invention the f-number selection is related to the frame rate. The lower the f-number, the lower the frame rate. In the currently preferred embodiment, imaging parameters are derived for a variety of f numbers. Each f-number corresponds to a different frame rate for the imaging system. Therefore, in the currently preferred embodiment, the f-number is selected accordingly by selecting the frame rate. For instance, an f-number of 1.5 is selected by choosing a low frame rate. (A low frame rate does, however, produce a high resolution.) Similarly, an f-number of 3.0 is selected by choosing a high frame rate. (A high frame rate produces a lower resolution). Thus, the sonographer may select the appropriate resolution and frame rate according to the particular application.

ESTIMATE THE TRANSMIT FREQUENCY CURVE

Once the f-number is selected, the transmit frequency curve is selected (processing block 302). One of the major advantages of the present invention is the optimization of transmit frequency within each transmit focal zone. Optimizing the transmit frequency, in conjunction with dynamic bandpass filtering of the received echo signals, allows for increased resolution at shallow depths, and increased penetration deep within a single image. Furthermore, the optimization also provides for the best drop-off characteristics for the pulse after the zone.

The higher the frequency, the better the temporal resolution. Characteristically, however, the higher the frequency of the ultrasonic waves, the lower the penetration into the body. Likewise, the lower the frequency, the greater the penetration into the body. By varying the transmit frequency as a function of the changing depths transmit zones, the present invention capitalizes on the inherent frequency attenuation effects of ultrasonic waves in the body. In the present invention, at shallow depths, where attenuation is not a problem, the transmit frequency can be set high in order to produce the highest resolution, while the frequency is set lower for deeper zones of ultrasonic wave.

Transmit frequency is estimated to produce the best penetration. In the currently preferred embodiment of the present invention, the transmit frequency which produces the best penetration is estimated by assuming that the transmitter produces a single unipolar pulse whose maximum voltage is fixed and produces pulses with a shape that is roughly Gaussian in nature. The effective frequency of the pulse is determined according to its temporal width. In the currently preferred embodiment, it is also assumed that the transducer can be modeled as having a linear transfer function from voltage derived to and from the acoustic energy. Finally, the currently preferred embodiment assumes that the anelastic attenuation in the body (i.e., the average value of tissue attenuation) is represented by a constant "Q". Under these assumptions, the spectrum of a pulse travelling to the bottom of the focal zone and back (i.e., a round trip journey) is the product of the frequency spectrum of the pulse, the two way transfer function, and the two way attenuation curve.

If the transmit pulse has a width $\sigma$, then the amplitude of its spectrum is proportional to:

$$\frac{1}{\sigma_f} e^{-\frac{f^2}{2\sigma_f^2}}$$

where $\sigma_f = 1/(2\pi\sigma_1)$ is the effective frequency of the pulse. For a center frequency $f_0$ and a bandwidth $\sigma_0$ of the probe, the resulting waveform or pulse before attenuation has a frequency spectrum proportional to:

$$\frac{1}{\sigma_f} e^{-\frac{f^2}{2\sigma_f^2}} \times e^{-\frac{f-f_0^2}{2\sigma_0^2}}$$

The expression above can be reduced to a Gaussian of the form:

$$A_1 e^{-\frac{(f-f_1)^2}{2\sigma_1^2}}$$

with $$\sigma_1^2 = \frac{\sigma_f^2 \sigma_0^2}{\sigma_f^2 + \sigma_0^2}$$

$$f_1 = \frac{f_0 \sigma_1^2}{\sigma_0^2} = f_0 \frac{\sigma_f^2}{\sigma_0^2 + \sigma_f^2}$$

and:

$$A_1 = \frac{1}{\sigma_f} e^{-\frac{f_0^2}{2(\sigma_0^2 + \sigma_f^2)}}$$

The effect of the attenuation is to shift this response to another Gaussian. Including effect of the attenuation results in a frequency spectrum represented by:

$$A_1 e^{-\frac{(f-f_1)^2}{2\sigma_1^2}} e^{-\alpha z |f|}$$

where $\alpha$ is the attenuation parameter and $z$ is the depth of the focal zone. Assuming $\alpha z \sigma_1^2 < f_1$, the final frequency spectrum is represented by:

$$A_2 e^{-\frac{(f-f_2)^2}{2\sigma_2^2}}$$

where:

$$A_2 = A_1 e^{\frac{-2\alpha z f_1 + (\alpha z \sigma_1)^2}{2}} = \frac{1}{\sigma_f} e^{-\frac{f_0^2 + 2\alpha z \sigma_f^2 f_0 - (\alpha z \sigma_0 \sigma_f)^2}{2(\sigma_0^2 + \sigma_f^2)}}$$

$$f_2 = f_1 - \alpha z \sigma_1^2 = (f_0 - \alpha z \sigma_0^2) \left( \frac{\sigma_f^2}{\sigma_0^2 + \sigma_f^2} \right)$$

$$\sigma_2^2 = \sigma_1^2 = \frac{\sigma_0^2 \sigma_f^2}{\sigma_0^2 + \sigma_f^2}$$

The amplitude of the time domain pulse (ignoring dispersion) is proportional to:

$$A_2 \sigma_2 = \frac{\sigma_0}{\sqrt{\sigma_0^2 + \sigma_f^2}} e^{-\frac{f_0^2 + 2\alpha z \sigma_2^2 f_0 - (\alpha z \sigma_0 \sigma_f)^2}{2(\sigma_0^2 + \sigma_f^2)}}$$

The transmit pulse frequency width $\sigma_{amp}$ that maximizes this amplitude is then given by the equation:

$$\sigma_{amp}^2 = f_0^2 - \sigma_0^2 (1 + 2\alpha z f_0 - (\alpha z \sigma_0)^2)$$

and the resulting maximum amplitude (normalized to $z=0$) and associated frequency for the zone becomes:

$$A_{amp} \propto \frac{1}{1 - az\sigma_0\left(\frac{\sigma_0}{f_0}\right)} e^{-\frac{-2az f_0 + (az\sigma_0)^2}{2}}$$

$$f_{amp} = f_0\left(1 - \left(\frac{\sigma_0}{f_0}\right)^2 - az\sigma_0\left(\frac{\sigma_0}{f_0}\right)\right)$$

FIG. 4 shows an example of the estimated frequency curve using the above approximations, the transmitter frequency $\sigma_{amp}$ and the center frequency of the received pulse $f_{amp}$ as a function of transmit zone depth for a probe having a 7.5 MHz center frequency $f_0$ and 66% bandwidth (i.e., $\sigma_0 \approx 2.0$ MHz). Referring to FIG. 4, above a certain depth, shown as 4 cm, the signal pulse has sufficient amplitude, $A_{enough}$, to fully utilize the dynamic range of the display. Above this depth, it is advantageous to raise the transmit frequency in order to improve resolution. Assuming $\sigma_f > \sigma_0$, the best resolution is obtained with a transmit pulse of $$\sigma_{res} = \frac{A_{amp}(0)}{A_{enough}} e^{-az f_0}$$

where $A_{amp}(0)$ is the maximum amplitude at $z=0$. In actuality, this is not a severe constraint on the transmit frequency. As FIG. 4 depicts, while the above expressions for $\sigma_{amp}$ and $\sigma_{res}$ are useful for setting the transmit frequencies, the actual center frequency received at the probe varies only slightly from the simple case of $\sigma_f \to \infty$, or $$f_\infty = f_0\left(1 - az\sigma_0\left(\frac{\sigma_0}{f}\right)\right)$$

In other words, the center frequency of the transmitted pulse (shown as the thick curve) varies only slightly from the case of broad band excitation, $f_\infty$.

In sum, the transmit frequency is lowered for deep zones to increase the energy of the returning signal, while in shallow zones, the transmit frequency is raised to improve resolution, maintain a constant signal strength and insure rapid attenuation below the focal zone.

In actuality, more elaborate pulse control allows even greater flexibility in adjusting the transmit frequency characteristics. However, any pulse control scheme subsequently used must calculate according to the center frequency of the pulse after two-way travel. Since the optimization of transmit pulse characteristics has only a moderate effect on this frequency function, the full bandwidth approximation $f_\infty$, below, can be used.

$$f_\infty = f_0\left(1 - az\sigma_0\left(\frac{\sigma_0}{f_0}\right)\right)$$

in the estimation of zone boundaries, where $\alpha$ is the attenuation constant (roughly 1 dB/(cm MHz)) and z is the depth to the center of the zone.

SELECT THE ZONE BOUNDARIES

Once the frequency curve has been established, the zone boundaries must be selected (processing block 303). In essence, selecting the zone boundaries, selects the number of zones. It should be noted that the number and size of the zones can be chosen according to the specific application of the ultrasonic imaging system. It is convenient to characterize the behavior of the beam near the focus by the average phase error $\Phi$ on the zone boundaries. Fixing the phase error to be the same at every zone boundary guarantees a bound on the variation in the beam width, and continuity of the beam across the boundaries.

One goal of the present invention is to maintain consistent focal quality over an extended region of depth in an ultrasound image. To maintain consistent focal quality, the system's minimum lateral resolution, or spot size, undergoes only small, smooth variations with depth. As stated previously, since each transmit zone has a single frequency and aperture size, the size of the transmit zones must remain "small". By specifying a maximum average phase error on the zone boundaries, specific limits on the variations on the lateral extent of the impulse response (i.e., the spot size) are set.

FIG. 5 illustrates a transducer 51 in relationship to a focal point 52. Transducer 51 is aligned with focal point 52, such that the focal point 52 is distance z away from transducer 51. Furthermore, one of the elements of the array located a distance x away from the center of the transducer is a distance r from focal point 52. Referring to FIG. 5, assuming geometric acoustics, the delay d (x) (expressed in units of length) required to focus a beam at a depth z is given by the equation:

$$d(x) = z - \sqrt{r^2 - z^2}$$

Or for $x/z << 1$:

$$d(x) \approx \frac{1}{2} \frac{x^2}{z}$$

The delay errors e (x, $\Delta z$) at a depth $z + \Delta z$ due to this delay profile would then be represented by:

$$e(x, dz) \approx \frac{1}{2} \frac{x^2}{(z + \Delta z)} - \frac{1}{2} \frac{x^2}{z}$$

or where $\Delta z$ is small:

$$e(x, \Delta z) \approx \frac{1}{2} \frac{x^2}{z^2} \Delta z$$

This delay error, averaged over the aperture, is a measure of how far out of focus a beam is. For a one-dimensional aperture of length, the average delay error D ($\Delta z$) becomes:

$$D(\Delta z) = \frac{1}{a} \int_{-a/2}^{a/2} dx \left(\frac{1}{2} \frac{x^2}{z^2} \Delta z\right) = \frac{1}{24} \frac{\Delta z}{f^2}$$

where $f = z/a$ is the f-number at the focal point. If the relative phase error $\Phi$ is defined as the ratio between this delay error expressed as a fraction of wavelength $\lambda$ of the center frequency of the transmitted pulse, then the relative pulse error $\Phi$ is represented by the equation:

$$\Phi = \frac{1}{24} \frac{\Delta z}{f^2 \lambda}$$

where $\Delta z$ is the distance from the center of the zone to the zone boundary, f is the f-number, lambda $= c/f\infty$) is the wavelength of the pulse and c is the velocity of sound.

Selecting transmit zone sizes that limit this phase error restricts the variations in the amplitude and axial resolution of the beam. In the currently preferred embodiment, the "depth of focus" of a beam is defined as twice the distance between the focal point and the depth where the beam is laterally broader by a factor of $\sqrt{2}$. Using $3f^2\lambda$ to represent the depth of focus, and assuming the beam spreads quadratically near the focus, then the beam width is approximately:

$$b \approx b_0 \left(1 + (\sqrt{2} - 1)\left(\frac{\Delta z}{\frac{3}{2} f^2 \lambda}\right)\right)$$

where $b_0$ is the beam width at the focal point. In terms of the relative phase error $\Phi$, the fractional change in the beam width is approximately given by the equation:

$$\frac{b - b_0}{b_0} = (10\Phi)^2$$

For example, according to the above expression, a maximum phase error of 0.05 guarantees that the spot size will not vary by more than 25% in the zone. A similar relationship holds for the fractional change in beam intensity.

Again, comprises must be made between image quality and frame rate. Small phase errors produce very smooth beams. For large f numbers, small phase errors can be used because the zones are large. Because of the large zones, the frame rate will be higher. Small f numbers require smaller zones. Because of the small zones, the frame rate will be lower. Therefore, to improve the lower frame rate, the phase errors can be made larger. In the currently preferred embodiment, the phase errors are kept small and constant at the zone boundaries. By doing this, banding is prevented and, thus, image quality improves.

Given the f-number, frequency function, and the phase error, the position of the zone boundaries and the aperture size for each zone can be calculated by the following algorithm. Given the location of the top of the first zone, the bottom of the zone is incremented in small amounts of distance, effectively lengthening the zone. For each increment to the zone depth, the center frequency, aperture size and associated phase error are calculated according to the bottom of the zone. The deepest zone boundary that does not exceed the allowable phase error becomes the end of the zone and, therefore, the top of the next zone. This method is repeated until the maximum desired depth has been reached or the maximum number of zones has been exceeded.

In the currently preferred embodiment, the above steps to generate the zones boundaries are accomplished using a computer program. In the currently preferred embodiment, the computer program is written in the programming language "C" and is contained in Appendix B. A typical output list is also included in Appendix B.

ADJUSTMENTS

These "first pass" estimates for the imaging parameters are sufficient to produce good images. However, fine adjustments can compensate for effects not fully considered and accommodated up to this point (processing block 304).

One such adjustment involves out of plane energy. Linear arrays used in modern ultrasound imaging usually employ a lens that focuses the out of plane energy at a fixed depth. In the region of the fixed depth, the beam characteristics may change significantly from zone to zone. By decreasing the size of the zones in this region, the discontinuities are reduced in amplitude and beam width is reduced to an acceptable level. If the zone boundaries are moved, the aperture size must be recalculated for each zone. Therefore, the selection of f-number stop (301) must be repeated.

Another adjustment is made to compensate for the limits in aperture. At some depth in the image, all of the available aperture will be used. Below this depth, it is impossible to maintain a constant f-number. By maintaining a constant phase error in this region, the zones become large. In the currently preferred embodiment, a maximum zone size is usually determined heuristically and maintained below this depth.

Another adjustment that may be required is due to the inherent faults in utilizing approximations in the previously utilized derivations. Differences between the geometric focus and the actual acoustic focus of the transducer can cause the focus to be shifted slightly from the center of a zone. In the currently preferred embodiment, the center of the geometric focus is adjusted by hand in each zone until the brightest part of the beam is in the center of the zone to compensate for this difference. This also insures that the beam size is continuous across the zone boundaries.

The transmit frequencies in each zone may also be fine tuned to maximize resolution in the shallow zones and penetration in the deep zones. The transmit parameters can be modified to eliminate any noticeable gain discontinuity, if any, from zone to zone. This can usually be accomplished adjusting the transmit parameters which only limit the maximum depth of penetration. For example, in the currently preferred embodiment, if a zone is brighter than adjacent zone then the transmit frequency may be raised slightly in the bright zone to produce a smoother gain profile, without significantly affecting the beam width.

SETTING THE DELAY TIMES

After the zone boundaries have been set, the delay times for firing focused ultrasonic waves are determined (processing block 305). In any multi-zone transmit focusing scheme transmit bursts are fired in rapid succession along the same line. While receiving energy from a zone, energy returning from the previous pulse is returning from deeper in the body. Acoustic wave propagation energy is attenuated according to the equation:

$$\text{attenuation (dB)} \approx \alpha z f_0$$

Typically about 40 dB of signal is displayed in an ultrasound image. If the energy from the previous zone attenuates by 50 dB, a 10 dB "safety zone" to account for variations in scattering intensity in the body would exist. For example, with a 7.5 Mhz probe and a 1 dB/(cm Mhz) attenuation, each transmit line segment waits a time equivalent to 6.67 cm. For an image with this depth, the amount of dead time roughly doubles the time required to produce each frame as compared to the method employed by the present invention (i.e., firing immediately after the bottom of each zone has been received).

There are a number of factors that can modify the required dead time. One of the factors relates to when small f numbers are used. Zones which have a small f-number are the smallest and therefore are limited by frame rate. However, tightly focused beams diverge rapidly beyond the focal point. Therefore, the effective attenuation can be much greater than for the plane wave approximation. In addition, the transmit frequencies in the near zones are higher than in the deeper zones and diminish faster than the lower frequencies.

Application specific influences due to the physiology of the human body also influence delay times. For instance, when a probe is imaging a neck, there are no bright reflectors deep in the image, so the 10 dB guard band is not required. On the other hand, when imaging the heart or the abdomen, deep interfaces exist that are strong reflectors. In this case a 10 dB guard band may not be enough.

In the currently preferred embodiment, the critical delay time parameter is initially set to the 50 dB level based on the center frequency of the probe. This level is then varied until the maximum acceptable artifact is seen during clinical applications. In effect, the level is lowered. It should be noted that the critical time delays are different for different applications.

SELECT NUMBER OF SIMULTANEOUS ZONES

Once the delay times have been set, the number of simultaneous zones are selected (processing block 306). Ideally, every transmit zone within the depth of an image would be used to produce that image. However, the frame rates currently are limiting. In most applications, there is a region of interest where a continuous focus is desirable, but above and below that region lower quality focusing can be tolerated. Generally for each f-number, and potentially for each application, a different number of simultaneous zones is selected. Since the zones are smaller for lower f numbers, more zones are required to generate each line in order to maintain a reasonable range of in-focus depth.

SELECTION OF THE LINE DENSITY

Next, the line density is selected (processing block 307). The standard line spacing for linear array probes is equal to the element spacing of the probe, one line per element. A simple option known as half-line scanning doubles this density to 2 lines per element. Half-line scanning produces a better resolution, but also divides the frame rate by two. For high frequencies and low f numbers, the use of half-line scanning may be desirable to ensure proper spatial sampling. For example, estimating the beam width as $R\lambda$ for f/1.5 Mhz gives a minimum width of 0.46 mm. A 96 element 40 mm probe has an element spacing of about 0.42 mm. In this case, using standard line density (i.e., scanning) is likely to spatially alias the image.

If the frame rate for half-line scanning is below a pre-described minimum, then full line scanning is used. Using half-line versus full line is very application specific. For applications, such as vascular work in the neck, the frame rate can be set to the minimum rate that makes moving the probe and locating targets annoying, about 8-10 frames per second. Where detailed motion is important, such as the movement of values for cardiac applications, the frame rate might be set to 30 frames per second, the maximum refresh rate of the video display in the currently preferred embodiment. Similarly with respect to the delay times and number of simultaneous zones, clinical testing is required to evaluate the trade-offs between frame rate and the use of either half-line or full-line scanning.

Although these seven steps are presented in their most logical order they are clearly not independent. Furthermore, in some cases, it may be necessary to start the process over at a certain step and repeat the remaining steps in order to arrive at an acceptable solution.

FIGS. 6A, 6B and 6C show a comparison between conventional multi-zone focusing and the confocal imaging and precise imaging concentration of the present invention. Referring to FIG. 6A, the large zones and small f numbers in the conventional case cause large variation in the beam profile within each zone. Furthermore, the phase errors at the zone boundaries are varied, causing discontinuities in the beam width. It should be noted that the horizontal scale has been exaggerated for clarity. The average beam width of the f/3 confocal imaging example shown in FIG. 6B is about the same as in the converted multi-zone case as shown. However, the variations in the beam size are minimal and the continuity on the zone boundaries is guaranteed by a constant phase error and the fine adjustment of the focal positions generated according to the present invention.

The f/1.5 confocal imagining example shown in FIG. 6C illustrates a tight, smooth, essentially continuous beam. The gain in resolution in the shallow zones in the confocal image of the present invention results from optimizing the transmit frequency in each zone.

The currently preferred embodiment of the confocal imaging of the present invention uses a constant f-number throughout the image, small constant phase errors at the zone boundaries, zone dependent transmit frequencies, depth dependent received filtering, and careful adjustment of the focal position within each zone. By using the above, a smooth seamless beam pattern is generated.

Whereas many alterations and modifications of the present invention will no doubt become apparent to a person of ordinary skill in the art after having read the foregoing description, it is to be understood that the particular embodiment shown and described by illustration are in no way intended to be considered limiting. Therefore, reference to the details of the preferred embodiments are not intended to limit the scope of the claims which themselves recite only those features regarded as essential to the invention.

Thus, a method and means for continuously focusing the ultrasonic waves during transmit and receive has been described.

APPENDIX A

```
/*m
*******************************************************************
*
*   @(#)p160.cfisrc    1.4 3/2/92
*
*   Probe table data for the LA/7.5/40.
*
*******************************************************************
m*/ probe.foc_sel = 2;              /* Focus step                       */
    probe.xmit_zone = 2;            /* Initial transmit zone number     */

/*                  focus selections - definitions                      */
    probe.zone_values[0] = 1;       /* default zone number for mixed    */
                                    /* modes                            */
    probe.zone_values[1] = 3;       /* default zone number for focus    */
                                    /* select A                         */
    probe.zone_values[2] = 5;       /* default zone number for focus    */
                                    /* select B                         */
    probe.zone_values[3] = 7;       /* default zone number for focus    */
                                    /* select C                         */
    probe.zone_values[4] = 9;       /* default zone number for focus    */
                                    /* select D                         */

/*              1=micro-steering; 0=odd/even apertures                  */
    probe.micro_steer[0] = 0;       /* default halfline scanning for    */
                                    /* mixed modes                      */
    probe.micro_steer[1] = 0;       /* default halfline scanning for    */
                                    /* focus select A                   */
    probe.micro_steer[2] = 0;       /* default halfline scanning for    */
                                    /* focus select B                   */
    probe.micro_steer[3] = 0;       /* default halfline scanning for    */
                                    /* focus select C                   */
    probe.micro_steer[4] = 1;       /* default halfline scanning for    */
                                    /* focus select D                   */

/*       region of focus * static_foc / 100 >= fov then static foc      */
    probe.static_foc[0] = 0;        /* static focus trigger for mixed   */
                                    /* modes                            */
    probe.static_foc[1] = 0;        /* static focus trigger for focus   */
                                    /* select A                         */
    probe.static_foc[2] = 90;       /* static focus trigger for focus   */
                                    /* select B                         */
    probe.static_foc[3] = 90;       /* static focus trigger for focus   */
                                    /* select C                         */
    probe.static_foc[4] = 90;       /* static focus trigger for focus   */
                                    /* select D                         */
/*                      ICON DEPENDENT ITEMS                            */
/*                                                                      */

/* Icon dependent transmit zone number                              */
    probe.xmit_zone_icon[ 0] = 11;   probe.xmit_zone_icon[ 1] = 7;
    probe.xmit_zone_icon[ 2] = 44;   probe.xmit_zone_icon[ 3] = 20;
    probe.xmit_zone_icon[ 4] = 20;   probe.xmit_zone_icon[ 5] = 3;
    probe.xmit_zone_icon[ 6] = 3;    probe.xmit_zone_icon[ 7] = 7;
    probe.xmit_zone_icon[ 8] = 20;   probe.xmit_zone_icon[ 9] = 20;
    probe.xmit_zone_icon[10] = 20;   probe.xmit_zone_icon[11] = 20;

/* Icon dependent transmit zone selection                           */
```

```
probe.foc_sel_icon[ 0] = 2;              probe.foc_sel_icon[ 1] = 3;
probe.foc_sel_icon[ 2] = 1;              probe.foc_sel_icon[ 3] = 1;
probe.foc_sel_icon[ 4] = 1;              probe.foc_sel_icon[ 5] = 2;
probe.foc_sel_icon[ 6] = 2;              probe.foc_sel_icon[ 7] = 2;
probe.foc_sel_icon[ 8] = 1;              probe.foc_sel_icon[ 9] = 1;
probe.foc_sel_icon[10] = 1;              probe.foc_sel_icon[11] = 0;

/* Icon dependent zone values                                                     */
probe.zone_values_icon[0][0] = 1;        probe.zone_values_icon[0][1] = 1;
probe.zone_values_icon[0][2] = 1;        probe.zone_values_icon[0][3] = 1;
probe.zone_values_icon[0][4] = 1;        probe.zone_values_icon[0][5] = 1;
probe.zone_values_icon[0][6] = 1;        probe.zone_values_icon[0][7] = 1;
probe.zone_values_icon[0][8] = 1;        probe.zone_values_icon[0][9] = 1;
probe.zone_values_icon[0][10] = 1;       probe.zone_values_icon[0][11] = 1;

probe.zone_values_icon[1][0] = 3;        probe.zone_values_icon[1][1] = 3;
probe.zone_values_icon[1][2] = 3;        probe.zone_values_icon[1][3] = 3;
probe.zone_values_icon[1][4] = 3;        probe.zone_values_icon[1][5] = 3;
probe.zone_values_icon[1][6] = 3;        probe.zone_values_icon[1][7] = 3;
probe.zone_values_icon[1][8] = 3;        probe.zone_values_icon[1][9] = 3;
probe.zone_values_icon[1][10] = 3;       probe.zone_values_icon[1][11] = 3;

probe.zone_values_icon[2][0] = 5;        probe.zone_values_icon[2][1] = 5;
probe.zone_values_icon[2][2] = 5;        probe.zone_values_icon[2][3] = 5;
probe.zone_values_icon[2][4] = 5;        probe.zone_values_icon[2][5] = 5;
probe.zone_values_icon[2][6] = 5;        probe.zone_values_icon[2][7] = 5;
probe.zone_values_icon[2][8] = 5;        probe.zone_values_icon[2][9] = 5;
probe.zone_values_icon[2][10] = 5;       probe.zone_values_icon[2][11] = 5;

probe.zone_values_icon[3][0] = 7;        probe.zone_values_icon[3][1] = 7;
probe.zone_values_icon[3][2] = 7;        probe.zone_values_icon[3][3] = 7;
probe.zone_values_icon[3][4] = 7;        probe.zone_values_icon[3][5] = 7;
probe.zone_values_icon[3][6] = 7;        probe.zone_values_icon[3][7] = 7;
probe.zone_values_icon[3][8] = 7;        probe.zone_values_icon[3][9] = 7;
probe.zone_values_icon[3][10] = 7;       probe.zone_values_icon[3][11] = 7;

probe.zone_values_icon[4][0] = 9;        probe.zone_values_icon[4][1] = 9;
probe.zone_values_icon[4][2] = 9;        probe.zone_values_icon[4][3] = 9;
probe.zone_values_icon[4][4] = 9;        probe.zone_values_icon[4][5] = 9;
probe.zone_values_icon[4][6] = 9;        probe.zone_values_icon[4][7] = 9;
probe.zone_values_icon[4][8] = 9;        probe.zone_values_icon[4][9] = 9;
probe.zone_values_icon[4][10] = 9;       probe.zone_values_icon[4][11] = 9;

/* Icon dependent half line scanning                                              */
probe.micro_steer_icon[0][0] = 0;        probe.micro_steer_icon[0][1] = 0;
probe.micro_steer_icon[0][2] = 0;        probe.micro_steer_icon[0][3] = 0;
probe.micro_steer_icon[0][4] = 0;        probe.micro_steer_icon[0][5] = 0;
probe.micro_steer_icon[0][6] = 0;        probe.micro_steer_icon[0][7] = 0;
probe.micro_steer_icon[0][8] = 0;        probe.micro_steer_icon[0][9] = 0;
probe.micro_steer_icon[0][10] = 0;       probe.micro_steer_icon[0][11] = 0;

probe.micro_steer_icon[1][0] = 0;        probe.micro_steer_icon[1][1] = 1;
probe.micro_steer_icon[1][2] = 0;        probe.micro_steer_icon[1][3] = 0;
probe.micro_steer_icon[1][4] = 0;        probe.micro_steer_icon[1][5] = 0;
probe.micro_steer_icon[1][6] = 0;        probe.micro_steer_icon[1][7] = 0;
probe.micro_steer_icon[1][8] = 0;        probe.micro_steer_icon[1][9] = 0;
probe.micro_steer_icon[1][10] = 0;       probe.micro_steer_icon[1][11] = 0;

probe.micro_steer_icon[2][0] = 0;        probe.micro_steer_icon[2][1] = 1;
```

```
probe.micro_steer_icon[2][2] = 0;      probe.micro_steer_icon[2][3] = 0;
probe.micro_steer_icon[2][4] = 0;      probe.micro_steer_icon[2][5] = 0;
probe.micro_steer_icon[2][6] = 0;      probe.micro_steer_icon[2][7] = 0;
probe.micro_steer_icon[2][8] = 0;      probe.micro_steer_icon[2][9] = 0;
probe.micro_steer_icon[2][10] = 0;     probe.micro_steer_icon[2][11] = 0;

probe.micro_steer_icon[3][0] = 0;      probe.micro_steer_icon[3][1] = 1;
probe.micro_steer_icon[3][2] = 0;      probe.micro_steer_icon[3][3] = 0;
probe.micro_steer_icon[3][4] = 0;      probe.micro_steer_icon[3][5] = 0;
probe.micro_steer_icon[3][6] = 0;      probe.micro_steer_icon[3][7] = 0;
probe.micro_steer_icon[3][8] = 0;      probe.micro_steer_icon[3][9] = 0;
probe.micro_steer_icon[3][10] = 0;     probe.micro_steer_icon[3][11] = 0;

probe.micro_steer_icon[4][0] = 0;      probe.micro_steer_icon[4][1] = 1;
probe.micro_steer_icon[4][2] = 0;      probe.micro_steer_icon[4][3] = 0;
probe.micro_steer_icon[4][4] = 0;      probe.micro_steer_icon[4][5] = 0;
probe.micro_steer_icon[4][6] = 0;      probe.micro_steer_icon[4][7] = 1;
probe.micro_steer_icon[4][8] = 0;      probe.micro_steer_icon[4][9] = 0;
probe.micro_steer_icon[4][10] = 0;     probe.micro_steer_icon[4][11] = 0;

/* Icon dependent static focus trigger                                     */
probe.static_foc_icon[0][0] = 0;       probe.static_foc_icon[0][1] = 0;
probe.static_foc_icon[0][2] = 0;       probe.static_foc_icon[0][3] = 0;
probe.static_foc_icon[0][4] = 0;       probe.static_foc_icon[0][5] = 0;
probe.static_foc_icon[0][6] = 0;       probe.static_foc_icon[0][7] = 0;
probe.static_foc_icon[0][8] = 0;       probe.static_foc_icon[0][9] = 0;
probe.static_foc_icon[0][10] = 0;      probe.static_foc_icon[0][11] = 0;

probe.static_foc_icon[1][0] = 0;       probe.static_foc_icon[1][1] = 0;
probe.static_foc_icon[1][2] = 0;       probe.static_foc_icon[1][3] = 0;
probe.static_foc_icon[1][4] = 0;       probe.static_foc_icon[1][5] = 0;
probe.static_foc_icon[1][6] = 0;       probe.static_foc_icon[1][7] = 200;
probe.static_foc_icon[1][8] = 0;       probe.static_foc_icon[1][9] = 0;
probe.static_foc_icon[1][10] = 0;      probe.static_foc_icon[1][11] = 0;

probe.static_foc_icon[2][0] = 90;      probe.static_foc_icon[2][1] = 90;
probe.static_foc_icon[2][2] = 90;      probe.static_foc_icon[2][3] = 90;
probe.static_foc_icon[2][4] = 90;      probe.static_foc_icon[2][5] = 90;
probe.static_foc_icon[2][6] = 90;      probe.static_foc_icon[2][7] = 90;
probe.static_foc_icon[2][8] = 90;      probe.static_foc_icon[2][9] = 90;
probe.static_foc_icon[2][10] = 90;     probe.static_foc_icon[2][11] = 90;

probe.static_foc_icon[3][0] = 90;      probe.static_foc_icon[3][1] = 90;
probe.static_foc_icon[3][2] = 90;      probe.static_foc_icon[3][3] = 90;
probe.static_foc_icon[3][4] = 90;      probe.static_foc_icon[3][5] = 90;
probe.static_foc_icon[3][6] = 90;      probe.static_foc_icon[3][7] = 90;
probe.static_foc_icon[3][8] = 90;      probe.static_foc_icon[3][9] = 90;
probe.static_foc_icon[3][10] = 90;     probe.static_foc_icon[3][11] = 90;

probe.static_foc_icon[4][0] = 90;      probe.static_foc_icon[4][1] = 90;
probe.static_foc_icon[4][2] = 90;      probe.static_foc_icon[4][3] = 90;
probe.static_foc_icon[4][4] = 90;      probe.static_foc_icon[4][5] = 90;
probe.static_foc_icon[4][6] = 90;      probe.static_foc_icon[4][7] = 90;
probe.static_foc_icon[4][8] = 90;      probe.static_foc_icon[4][9] = 90;
probe.static_foc_icon[4][10] = 90;     probe.static_foc_icon[4][11] = 90;

/* Icon dependent half line scanning magic frame rate                      */
probe.hl_frate_icon[0][0][0] = 150;    probe.hl_frate_icon[0][0][1] = 150;
```

```
probe.hl_frate_icon[0][0][2] = 150; probe.hl_frate_icon[0][0][3] = 150;
probe.hl_frate_icon[0][0][4] = 150; probe.hl_frate_icon[0][0][5] = 150;
probe.hl_frate_icon[0][0][6] = 150; probe.hl_frate_icon[0][0][7] = 150;
probe.hl_frate_icon[0][0][8] = 150; probe.hl_frate_icon[0][0][9] = 150;
probe.hl_frate_icon[0][0][10] = 150;probe.hl_frate_icon[0][0][11] = 150;

probe.hl_frate_icon[0][1][0] = 150; probe.hl_frate_icon[0][1][1] = 150;
probe.hl_frate_icon[0][1][2] = 150; probe.hl_frate_icon[0][1][3] = 150;
probe.hl_frate_icon[0][1][4] = 150; probe.hl_frate_icon[0][1][5] = 150;
probe.hl_frate_icon[0][1][6] = 150; probe.hl_frate_icon[0][1][7] = 150;
probe.hl_frate_icon[0][1][8] = 150; probe.hl_frate_icon[0][1][9] = 150;
probe.hl_frate_icon[0][1][10] = 150;probe.hl_frate_icon[0][1][11] = 150;

probe.hl_frate_icon[0][2][0] = 150; probe.hl_frate_icon[0][2][1] = 150;
probe.hl_frate_icon[0][2][2] = 150; probe.hl_frate_icon[0][2][3] = 150;
probe.hl_frate_icon[0][2][4] = 150; probe.hl_frate_icon[0][2][5] = 150;
probe.hl_frate_icon[0][2][6] = 150; probe.hl_frate_icon[0][2][7] = 150;
probe.hl_frate_icon[0][2][8] = 150; probe.hl_frate_icon[0][2][9] = 150;
probe.hl_frate_icon[0][2][10] = 150;probe.hl_frate_icon[0][2][11] = 150;

probe.hl_frate_icon[1][0][0] = 150; probe.hl_frate_icon[1][0][1] = 4;
probe.hl_frate_icon[1][0][2] = 150; probe.hl_frate_icon[1][0][3] = 150;
probe.hl_frate_icon[1][0][4] = 150; probe.hl_frate_icon[1][0][5] = 150;
probe.hl_frate_icon[1][0][6] = 150; probe.hl_frate_icon[1][0][7] = 52;
probe.hl_frate_icon[1][0][8] = 150; probe.hl_frate_icon[1][0][9] = 150;
probe.hl_frate_icon[1][0][10] = 150;probe.hl_frate_icon[1][0][11] = 150;

probe.hl_frate_icon[1][1][0] = 150; probe.hl_frate_icon[1][1][1] = 150;
probe.hl_frate_icon[1][1][2] = 150; probe.hl_frate_icon[1][1][3] = 150;
probe.hl_frate_icon[1][1][4] = 150; probe.hl_frate_icon[1][1][5] = 150;
probe.hl_frate_icon[1][1][6] = 150; probe.hl_frate_icon[1][1][7] = 150;
probe.hl_frate_icon[1][1][8] = 150; probe.hl_frate_icon[1][1][9] = 150;
probe.hl_frate_icon[1][1][10] = 150;probe.hl_frate_icon[1][1][11] = 150;

probe.hl_frate_icon[1][2][0] = 150; probe.hl_frate_icon[1][2][1] = 150;
probe.hl_frate_icon[1][2][2] = 150; probe.hl_frate_icon[1][2][3] = 150;
probe.hl_frate_icon[1][2][4] = 150; probe.hl_frate_icon[1][2][5] = 150;
probe.hl_frate_icon[1][2][6] = 150; probe.hl_frate_icon[1][2][7] = 150;
probe.hl_frate_icon[1][2][8] = 150; probe.hl_frate_icon[1][2][9] = 150;
probe.hl_frate_icon[1][2][10] = 150;probe.hl_frate_icon[1][2][11] = 150;

probe.hl_frate_icon[2][0][0] = 150; probe.hl_frate_icon[2][0][1] = 2;
probe.hl_frate_icon[2][0][2] = 150; probe.hl_frate_icon[2][0][3] = 150;
probe.hl_frate_icon[2][0][4] = 150; probe.hl_frate_icon[2][0][5] = 150;
probe.hl_frate_icon[2][0][6] = 150; probe.hl_frate_icon[2][0][7] = 149;
probe.hl_frate_icon[2][0][8] = 150; probe.hl_frate_icon[2][0][9] = 150;
probe.hl_frate_icon[2][0][10] = 150;probe.hl_frate_icon[2][0][11] = 150;

probe.hl_frate_icon[2][1][0] = 150; probe.hl_frate_icon[2][1][1] = 150;
probe.hl_frate_icon[2][1][2] = 150; probe.hl_frate_icon[2][1][3] = 150;
probe.hl_frate_icon[2][1][4] = 150; probe.hl_frate_icon[2][1][5] = 150;
probe.hl_frate_icon[2][1][6] = 150; probe.hl_frate_icon[2][1][7] = 150;
probe.hl_frate_icon[2][1][8] = 150; probe.hl_frate_icon[2][1][9] = 150;
probe.hl_frate_icon[2][1][10] = 150;probe.hl_frate_icon[2][1][11] = 150;

probe.hl_frate_icon[2][2][0] = 150; probe.hl_frate_icon[2][2][1] = 150;
probe.hl_frate_icon[2][2][2] = 150; probe.hl_frate_icon[2][2][3] = 150;
probe.hl_frate_icon[2][2][4] = 150; probe.hl_frate_icon[2][2][5] = 150;
```

```
probe.hl_frate_icon[2][2][6] = 150; probe.hl_frate_icon[2][2][7] = 150;
probe.hl_frate_icon[2][2][8] = 150; probe.hl_frate_icon[2][2][9] = 150;
probe.hl_frate_icon[2][2][10] = 150;probe.hl_frate_icon[2][2][11] = 150;

probe.hl_frate_icon[3][0][0] = 150; probe.hl_frate_icon[3][0][1] = 2;
probe.hl_frate_icon[3][0][2] = 150; probe.hl_frate_icon[3][0][3] = 150;
probe.hl_frate_icon[3][0][4] = 150; probe.hl_frate_icon[3][0][5] = 150;
probe.hl_frate_icon[3][0][6] = 150; probe.hl_frate_icon[3][0][7] = 8;
probe.hl_frate_icon[3][0][8] = 150; probe.hl_frate_icon[3][0][9] = 150;
probe.hl_frate_icon[3][0][10] = 150;probe.hl_frate_icon[3][0][11] = 150;

probe.hl_frate_icon[3][1][0] = 150; probe.hl_frate_icon[3][1][1] = 150;
probe.hl_frate_icon[3][1][2] = 150; probe.hl_frate_icon[3][1][3] = 150;
probe.hl_frate_icon[3][1][4] = 150; probe.hl_frate_icon[3][1][5] = 150;
probe.hl_frate_icon[3][1][6] = 150; probe.hl_frate_icon[3][1][7] = 150;
probe.hl_frate_icon[3][1][8] = 150; probe.hl_frate_icon[3][1][9] = 150;
probe.hl_frate_icon[3][1][10] = 150;probe.hl_frate_icon[3][1][11] = 150;

probe.hl_frate_icon[3][2][0] = 150; probe.hl_frate_icon[3][2][1] = 150;
probe.hl_frate_icon[3][2][2] = 150; probe.hl_frate_icon[3][2][3] = 150;
probe.hl_frate_icon[3][2][4] = 150; probe.hl_frate_icon[3][2][5] = 150;
probe.hl_frate_icon[3][2][6] = 150; probe.hl_frate_icon[3][2][7] = 150;
probe.hl_frate_icon[3][2][8] = 150; probe.hl_frate_icon[3][2][9] = 150;
probe.hl_frate_icon[3][2][10] = 150;probe.hl_frate_icon[3][2][11] = 150;

probe.hl_frate_icon[4][0][0] = 150; probe.hl_frate_icon[4][0][1] = 3;
probe.hl_frate_icon[4][0][2] = 150; probe.hl_frate_icon[4][0][3] = 150;
probe.hl_frate_icon[4][0][4] = 150; probe.hl_frate_icon[4][0][5] = 150;
probe.hl_frate_icon[4][0][6] = 150; probe.hl_frate_icon[4][0][7] = 9;
probe.hl_frate_icon[4][0][8] = 150; probe.hl_frate_icon[4][0][9] = 150;
probe.hl_frate_icon[4][0][10] = 150;probe.hl_frate_icon[4][0][11] = 150;

probe.hl_frate_icon[4][1][0] = 150; probe.hl_frate_icon[4][1][1] = 150;
probe.hl_frate_icon[4][1][2] = 150; probe.hl_frate_icon[4][1][3] = 150;
probe.hl_frate_icon[4][1][4] = 150; probe.hl_frate_icon[4][1][5] = 150;
probe.hl_frate_icon[4][1][6] = 150; probe.hl_frate_icon[4][1][7] = 150;
probe.hl_frate_icon[4][1][8] = 150; probe.hl_frate_icon[4][1][9] = 150;
probe.hl_frate_icon[4][1][10] = 150;probe.hl_frate_icon[4][1][11] = 150;

probe.hl_frate_icon[4][2][0] = 150; probe.hl_frate_icon[4][2][1] = 150;
probe.hl_frate_icon[4][2][2] = 150; probe.hl_frate_icon[4][2][3] = 150;
probe.hl_frate_icon[4][2][4] = 150; probe.hl_frate_icon[4][2][5] = 150;
probe.hl_frate_icon[4][2][6] = 150; probe.hl_frate_icon[4][2][7] = 150;
probe.hl_frate_icon[4][2][8] = 150; probe.hl_frate_icon[4][2][9] = 150;
probe.hl_frate_icon[4][2][10] = 150;probe.hl_frate_icon[4][2][11] = 150;

/* Icon dependent min reverb time                                           */
probe.min_reverb_db[0][0] = 50;      probe.min_reverb_db[0][1] = 50;
probe.min_reverb_db[0][2] = 50;      probe.min_reverb_db[0][3] = 50;
probe.min_reverb_db[0][4] = 50;      probe.min_reverb_db[0][5] = 50;
probe.min_reverb_db[0][6] = 50;      probe.min_reverb_db[0][7] = 50;
probe.min_reverb_db[0][8] = 50;      probe.min_reverb_db[0][9] = 50;
probe.min_reverb_db[0][10] = 50;     probe.min_reverb_db[0][11] = 50;

probe.min_reverb_db[1][0] = 50;      probe.min_reverb_db[1][1] = 11;
probe.min_reverb_db[1][2] = 50;      probe.min_reverb_db[1][3] = 50;
```

```
probe.min_reverb_db[1][4] = 50;        probe.min_reverb_db[1][5] = 50;
probe.min_reverb_db[1][6] = 50;        probe.min_reverb_db[1][7] = 50;
probe.min_reverb_db[1][8] = 50;        probe.min_reverb_db[1][9] = 50;
probe.min_reverb_db[1][10] = 50;       probe.min_reverb_db[1][11] = 50;

probe.min_reverb_db[2][0] = 50;        probe.min_reverb_db[2][1] = 11;
probe.min_reverb_db[2][2] = 50;        probe.min_reverb_db[2][3] = 50;
probe.min_reverb_db[2][4] = 50;        probe.min_reverb_db[2][5] = 50;
probe.min_reverb_db[2][6] = 50;        probe.min_reverb_db[2][7] = 11;
probe.min_reverb_db[2][8] = 50;        probe.min_reverb_db[2][9] = 50;
probe.min_reverb_db[2][10] = 50;       probe.min_reverb_db[2][11] = 50;

probe.min_reverb_db[3][0] = 50;        probe.min_reverb_db[3][1] = 11;
probe.min_reverb_db[3][2] = 50;        probe.min_reverb_db[3][3] = 50;
probe.min_reverb_db[3][4] = 50;        probe.min_reverb_db[3][5] = 50;
probe.min_reverb_db[3][6] = 50;        probe.min_reverb_db[3][7] = 11;
probe.min_reverb_db[3][8] = 50;        probe.min_reverb_db[3][9] = 50;
probe.min_reverb_db[3][10] = 50;       probe.min_reverb_db[3][11] = 50;

probe.min_reverb_db[4][0] = 50;        probe.min_reverb_db[4][1] = 8;
probe.min_reverb_db[4][2] = 50;        probe.min_reverb_db[4][3] = 50;
probe.min_reverb_db[4][4] = 50;        probe.min_reverb_db[4][5] = 50;
probe.min_reverb_db[4][6] = 50;        probe.min_reverb_db[4][7] = 9;
probe.min_reverb_db[4][8] = 50;        probe.min_reverb_db[4][9] = 50;
probe.min_reverb_db[4][10] = 50;       probe.min_reverb_db[4][11] = 50;
```

APPENDIX B

```
        fscale = alpha*s0*s0;
            izone    = 0;
        zone[izone]   = zmin;
        zone[izone+1] = zmin+minzs-1;
/* loop over zones */
        while((izone < nzones) && (zone[izone+1] <= zmax)){
/* loop over zone bottom */
            per = 0;
            while((per < phi) && (zone[izone+1] < (zmax+maxzs))){
/* calcuate test values for center of zone, freq and wavelength,
   and number of elements */
                zone[izone+1] += zstep;
                zmid  = .5*(zone[izone] + zone[izone+1]);
                freq  = f0 - fscale*zmid;
                lambda = c / (freq * 1000.);
                temp  = zmid / (f*pitch);
                nel   = .5*temp + .5;
                if(nel < 1)nel = 1;
                if(nel > nchan/2){
                    nel = nchan/2;
                    realf = zmid / (2.*pitch*nel);
                } else {
                    realf = f;
                }
/* calculate phase error on actual aperture */
                per    = 0.;
                for(iel=0; iel<nel; iel++){
                    x = (iel + .5)*pitch;
                    per += x*x*(1./zmid - 1./(float)zone[izone+1]);
                }
                per = .5*per / (nel*lambda);
```

```
/* estimate phase error for canstant f number */
            temp = (zone[izone+1]-zmid)/(24.*realf*realf*lambda);
            if(ecalc == 1)per = temp;
        }
        apsize[izone]   = 2*nel;
        zone [izone+1] -= zstep;
/* fix zone sizes if out of bounds */
        zdiff = zone[izone+1] - zone[izone];
        if(zdiff < minzs)zone[izone+1] = zone[izone] + minzs;
        if(zdiff > maxzs)zone[izone+1] = zone[izone] + maxzs;

izone++;
        zone[izone+1] = zone[izone];
    }
/* print out results */
    printf("CONFOCAL TRANSMIT ZONES\n\n");
    printf("transmit freq       = %1.2f MHz\n",f0);
    printf("bandwidth (1 s.d.)  = %1.2f MHz\n",s0);
    printf("f number            = %1.2f\n",f);
    printf("phase error         = %1.2f\n\n",phi);
    printf("   zone    min     max    apsize\n\n");
    for(i=0; i<izone; i++){
        printf(" %6d  %6d  %6d  %6d\n",i,zone[i],zone[i+1],apsize[i]);
    }
}
```

APPENDIX C: Typical computer output

CONFOCAL TRANSMIT ZONES transmit freq       = 7.50 MHz
bandwidth (1 s.d.)  = 2.00 MHz
f number            = 2.00
phase error         = 0.15

| zone | min | max | apsize |
|------|-----|-----|--------|
| 0    | 1   | 6   | 4      |
| 1    | 6   | 12  | 12     |
| 2    | 12  | 18  | 18     |
| 3    | 18  | 24  | 26     |
| 4    | 24  | 30  | 32     |
| 5    | 30  | 36  | 40     |
| 6    | 36  | 42  | 48     |
| 7    | 42  | 51  | 48     |
| 8    | 51  | 61  | 48     |
| 9    | 61  | 71  | 48     |
| 10   | 71  | 81  | 48     |

We claim:

1. A method of focusing energy waves during transmission and reception into a body at a plurality of focal points, each of said focal points corresponding to a zone within said body, wherein said energy waves are transmitted from a source into said body according to a set of time delays and transmit parameters and are reflected from discontinuities within said body, said method comprising the steps of:

selecting a plurality of zones, wherein said plurality of zones have a plurality of focal points, wherein each of said plurality of focal points is within one of said plurality of zones;

optimizing the transmit frequency of the energy waves for each of said plurality of zones, such that the energy is localized at said plurality of focal points within said body;

optimizing the bandwidth of the energy waves for each of said plurality of zones, such that the energy is localized at said plurality of focal points within said body;

determining the time delays between transmission necessary to ensure that energy waves subsequently transmitted to one of said focal points do not interfere with the reception of reflected energy waves from the remaining of said plurality of focal points, and scanning the body along a plurality of scan lines with the energy waves that are transmitted and focused in each of the plurality of zones using the time delays, the transmit frequency and the bandwidth for each of the plurality of zones, such that the energy waves for each of the plurality of zones has a single frequency and bandwidth to localize the energy waves in each of the plurality of zones, wherein the reflected energy waves from zones outside any one of the plurality of zones are reduced in strength when transmitting energy waves to said one of the plurality of zones to avoid interference with the reflected energy waves from said one of the plurality of zones, such that all of the reflected energy waves along one of said plurality of scan lines from one of said plurality of zones is not received before transmitting energy waves to another of said plurality of zones along said one of said plurality of scan lines, such that an image of said object is generated according to said reflected energy waves received from each of the plurality of zones.

2. The method as in claim 1 wherein each of said steps is performed dynamically, such that said said energy waves are focused during transmission and reception in real-time.

3. The method as in claim 1 wherein said energy waves are ultrasonic waves, such that an ultrasound image is generated.

4. The method as in claim 1 wherein said step of optimizing comprises the step of increasing the frequency of said energy waves at depths in the near field of said object.

5. A method of focusing ultrasonic waves at a plurality of focal points and a plurality of lines in a body, each of said focal points corresponding to a zone within said body, wherein said waves are transmitted from a source into said body according to a set of time delays and transmit parameters and are reflected from discontinuities within said body, said method comprising the steps of:

selecting a plurality of zones, wherein said plurality of zones have a plurality of focal points, wherein each of said plurality of focal points is within one of said plurality of zones;

optimizing the transmit frequency of said ultrasonic waves for each of said plurality of zones by increasing the frequency of said waves at depths in the near field of said object, such that the ultrasonic waves are localized at said plurality of focal points within said body;

optimizing the bandwidth of said ultrasonic waves for each of said plurality of zones by increasing the frequency of said waves at depths in the near field of said object, such that the ultrasonic waves are localized at said plurality of focal points within said body;

determining the time delays between transmission necessary to ensure that ultrasonic waves subsequently transmitted to one of said focal points do not interfere with the reception of reflected ultrasonic waves from the remaining of said plurality of focal points, and scanning the body along a plurality of scan lines with the ultrasonic waves that are transmitted and focused in each of the plurality of zones using the time delays, the transmit frequency and the bandwidth for each of the plurality of zones, such that the ultrasonic waves for each of the plurality of zones has a single frequency and bandwidth to localize the ultrasonic waves in each of the plurality of zones, wherein the reflected ultrasonic waves from zones outside any one of the plurality of zones are reduced in strength when transmitting ultrasonic waves to said one of the plurality of zones to avoid interference with the reflected ultrasonic waves from said one of said plurality of zones, such that all of the reflected ultrasonic waves along one of said plurality of scan lines from one of said plurality of zones is not received before transmitting ultrasonic waves to another of said plurality of zones along said one of said plurality of scan lines, such that an image of said object is generated according to said reflected ultrasonic waves.

6. The method as in claim 5 wherein each of said steps is performed dynamically, such that said said energy waves are focused during transmission and reception in real-time.

7. The method as in claim 5 further comprising the step of optimizing the intensity of said waves for said plurality of zones by increasing the intensity of waves for the deeper of said plurality of zones.

8. The method as defined in claim 5 further comprising the step of performing mix line sequencing, such that after the reflected ultrasonic waves from one of said plurality of focal point on one of said lines is received, the ultrasonic waves are transmitted to one of said plurality of focal points on another of said lines.

9. The method as defined in claim 5 further comprising the step of maintaining constant and small phase errors at the boundaries between each of said plurality of zones, such that banding is prevented.

10. An apparatus for generating an image of an object having discontinuities comprising:

transmitter means for transmitting energy waves for imaging at a plurality of depths within said object, wherein the transmitter means includes means for optimizing the frequency of said energy waves for each of said plurality of depths and means for optimizing the bandwidth for each of said plurality of depths, wherein the transmitter means includes means for scanning the object along a plurality of scan lines with the energy waves, such that each of the plurality of depths has a single frequency and bandwidth to localize the energy waves at each of the plurality of depths, wherein the reflected energy waves from zones outside any one of the plurality of depths are reduced in strength when transmitting energy waves to said one of the plurality of depths to avoid interference with the reflected energy waves from said one of said plurality of depths, such that all of the reflected energy waves along one of said plurality of scan lines from one of said plurality of depths is not received before transmitting energy waves to another of said plurality of depths along said one of said plurality of scan lines. such that said waves are localized at said plurality of depths when transmitted during scanning of the object; and receiving means for receiving reflected energy waves corresponding to reflections of energy waves from the discontinuities within a given depth, wherein an image of said object is generated according to said reflected energy waves received by said receiving means.

11. The apparatus as defined in claim 10 wherein said transmitter means focuses said waves dynamically, such that the image of said object is generated in real-time.

12. The apparatus as defined in claim 10 wherein said transmitter means optimizes the frequency for each of said plurality of depths by varying said frequency with depth, such that the frequency is increased for depths nearer into said object.

13. An apparatus for generating an ultrasonic image of an object having discontinuities comprising:

transmitter means for transmitting ultrasonic waves for imaging at a plurality of depths within an object, wherein the transmitter means includes means for dynamically focusing said ultrasonic waves at said plurality of depths, said means for dynamically focusing said ultrasonic waves includes means for optimizing the frequency of said ultrasonic waves for each of the plurality of depths and means for optimizing the bandwidth for each of the plurality of depths, such that each of the plurality of depths has a single frequency and bandwidth to localize the energy waves at each of the plurality of depths, wherein the reflected ultrasonic waves from depths outside any one of the plurality of depths are reduced in strength when transmitting the ultrasonic waves to said one of the plurality of depths to avoid interference with the reflected ultrasonic waves from said one of the plurality of depths, wherein the frequency is varied for each of plurality of depths, such that the frequency of said ultrasonic waves is increased for depths nearer into said object in order to optimize the transmit frequency for each of said plurality of depths to localize the ultrasonic waves when transmitted during scanning of the object, wherein the transmitter means scans the object along a plurality of scan lines using the ultrasonic waves, such that all of the reflected energy waves along one of said plurality of scan lines from one of said plurality of depths is not received before transmitting energy waves to another of said plurality of depths along said one of said plurality of scan lines; and receiving means for receiving reflected ultrasonic waves corresponding to reflections of ultrasonic waves from the discontinuities within a given depth, wherein an image of said object is generated in real-time according to said reflected ultrasonic waves received by said receiving means.

14. The apparatus as defined in claim 13 wherein said receiving means dynamically focuses on the reflected ultrasonic waves.

15. The apparatus as defined in claim 13 wherein said transmitter means optimizes the intensity of said waves for said plurality of zones by increasing the intensity of waves for the deeper of said plurality of zones.

16. A method of focusing energy waves in a body at a plurality of focal points and a plurality of lines, each of said focal points corresponding to a zone within said body, wherein said waves are transmitted from a source into said body according to a set of time delays and transmit parameters and are reflected from discontinuities within said body, said method comprising the steps of:

selecting a plurality of zones, wherein said plurality of zones have a plurality of focal points, wherein each of said plurality of focal points is associated with one of said plurality of zones, such that the energy is focused at said plurality of focal points within said body;

optimizing the transmit frequency of the energy waves for each of said plurality of zones, such that the energy is localized at said plurality of focal points within said body;

optimizing the bandwidth of the energy waves for each of said plurality of zones, such that the energy is localized at said plurality of focal points within said body;

maintaining the aperture size of said waves, such that the size of said plurality of zones remains small during transmission; and determining the transmit time delays necessary to ensure that energy waves subsequently transmitted to one of said focal points do not interfere with the reception of reflected energy waves from the remaining of said plurality of focal points, and scanning the body along a plurality of scan lines with the energy waves that are transmitted and focused in each of the plurality of zones using the time delays, the transmit frequency and the bandwidth for each of the plurality of zones, such that the energy waves for each of the plurality of zones has a single frequency and bandwidth to localize the energy waves in each of the plurality of zones, wherein the reflected energy waves from zones outside any one of the plurality of zones are reduced in strength when transmitting energy waves to said one of the plurality of zones to avoid interference with the reflected energy waves from said one of said plurality of zones, such that all of the reflected energy waves along one of said plurality of scan lines from one of said plurality of zones is not received before transmitting energy waves to another of said plurality of zones along said one of said plurality of scan lines, wherein an image of said object is generated according to said reflected energy waves received from each of the plurality of zones.

17. The method as defined in claim 16 wherein said step of maintaining comprises maintaining a low and constant f-number.

18. The method as defined in claim 16 wherein the aperture size for transmitting the energy waves is limited to a maximum available aperture and wherein said step of maintaining further comprises the step of making the zones larger once the maximum available aperture has been used.

19. The method as defined in claim 16 further comprising the step of performing mix line sequencing, such that after the reflected energy waves from one of said plurality of focal points on one of said lines is received, the energy waves are transmitted to one of said plurality of focal points on another of said lines.

20. A method of focusing energy waves into a body at a plurality of focal points, each of said focal points corresponding to a zone within said body, wherein said waves are transmitted from a source into said body according to a set of time delays and transmit parameters and are reflected from discontinuities within said body, said method comprising the steps of:

selecting a plurality of zones, wherein said plurality of zones have a plurality of focal points, wherein each of said plurality of focal points is associated with one of said plurality of zones, such that the energy is localized at said plurality of focal points within said body;

optimizing the transmit frequency of the energy waves for each of said plurality of zones, such that the energy is localized at said plurality of focal points within said body;

optimizing the bandwidth of the energy waves for each of said plurality of zones, such that the energy is localized at said plurality of focal points within said body;

maintaining the aperture size of said waves, such that the size of said plurality of zones remains small during transmission;

determining the time delays between transmission necessary to ensure that energy waves subsequently transmitted to one of said focal points do not interfere with the reception of reflected energy waves from the remaining of said plurality of focal points; and scanning the body along a plurality of scan lines with the energy waves that are transmitted and focused in each of the plurality of zones using the time delays, the transmit frequency and the bandwidth for each of the plurality of zones, such that the energy waves for each of the plurality of zones has a single frequency and bandwidth to localize the energy waves in each of the plurality of zones, wherein the reflected energy waves from zones outside any one of the plurality of zones are reduced in strength when transmitting energy waves to said one of the plurality of zones to avoid interference with the reflected energy waves from said one of the plurality of zones, such that all of the reflected energy waves along one of said plurality of scan lines from one of said plurality of zones is not received before transmitting energy waves to another of said plurality of zones along said one of said plurality of scan lines, wherein the step of scanning includes the step of selectively filtering the reflected energy waves during reception, such that an image of said object is generated according to said reflected energy waves.

21. The method as defined in claim 20 wherein said step of filtering comprises the step of filtering the low frequencies of said reflected energy waves for each of said plurality of zones.

22. A method of focusing energy waves in a body at a plurality of focal points, each of said focal points corresponding to a zone within said body, wherein said waves are transmitted from a source into said body according to a set of time delays and transmit parameters and are reflected from discontinuities within said body, said method comprising the steps of:

selecting a plurality of zones, wherein said plurality of zones have a plurality of focal points, wherein each of said plurality of focal points is associated with one of said plurality of zones;

optimizing the transmit frequency of the energy waves for each of said plurality of zones, such that the energy is localized at said plurality of focal points within said body;

varying the bandwidth of said waves for each of said plurality of zones during transmission, such that the energy is localized at said plurality of focal points within said body, wherein said step of varying said bandwidth comprises the step of varying the burst length of said waves during transmission;

maintaining the aperture size of said waves, such that the size of said plurality of zones remains small during transmission; and determining the time delays necessary to ensure that energy waves subsequently transmitted to one of said focal points do not interfere with the reception of reflected energy waves from the remaining of said plurality of focal points, and scanning the body along a plurality of scan lines with the energy waves that are transmitted and focused in each of the plurality of zones using the time delays, the transmit frequency and the bandwidth for each of the plurality of zones, such that the energy waves for each of the plurality of zones has a single frequency and bandwidth to localize the energy waves in each of the plurality of zones, wherein the reflected energy waves from zones outside any one of the plurality of zones are reduced in strength when transmitting energy waves to said one of the plurality of zones to avoid interference with the reflected energy waves from said one of the plurality of zones, such that all of the reflected energy waves along one of said plurality of scan lines from one of said plurality of zones is not received before transmitting energy waves to another of said plurality of zones along said one of said plurality of scan lines, wherein the step of scanning includes the step of receiving the reflected energy waves, such that an image of said object is generated according to said reflected energy waves.

23. The method as in claim 22 wherein each of said steps is performed dynamically, such that said said energy waves are focused during transmission and reception in real-time.

24. The method as in claim 22 wherein said energy waves are ultrasonic waves, such that an ultrasound image is generated.

25. The method as in claim 22 wherein said step of varying the burst length comprises the step of reducing the burst length of said waves at depths in the near field of said object.

26. The method as in claim 22 further comprising the step of optimizing the intensity of said energy waves for said plurality of zones by increasing the intensity of said energy waves for the deeper of said plurality of zones.

27. A method of focusing ultrasonic waves in a body at a plurality of focal points and a plurality of lines, each of said focal points corresponding to a zone within said body, wherein said waves are transmitted from a source into said body according to a set of time delays and transmit parameters and are reflected from discontinuities within said body, said method comprising the steps of:

selecting a plurality of zones, wherein said plurality of zones have a plurality of focal points, wherein each of said plurality of focal points is associated with one of said plurality of zones;

optimizing the transmit frequency of the ultrasonic waves for each of said plurality of zones, such that the ultrasonic waves are localized at said plurality of focal points within said body;

optimizing the bandwidth of said ultrasonic waves for each of said plurality of zones by reducing the burst length of said waves at depths in the near field of said object, such that the ultrasonic waves is localized at said plurality of focal points within said body;

maintaining the aperture size of said waves, such that the size of said plurality of zones remains small during transmission;

determining the time delays necessary to ensure that ultrasonic waves subsequently transmitted to one of said focal points do not interfere with the reception of reflected ultrasonic waves from the remaining of said plurality of focal points, and scanning the body along a plurality of scan lines with the ultrasonic waves that are transmitted and focused in each of the plurality of zones using the time delays, the transmit frequency and the bandwidth for each of the plurality of zones, such that the ultrasonic waves for each of the plurality of zones has a single frequency and bandwidth to localize the ultrasonic waves in each of the plurality of zones, wherein the reflected ultrasonic waves from zones outside any one of the plurality of zones are reduced in strength when transmitting ultrasonic waves to said one of the plurality of zones to avoid interference with the reflected ultrasonic waves of said one of the plurality of zones, such that all of the reflected ultrasonic waves along one of said plurality of scan lines from one of said plurality of zones is not received before transmitting ultrasonic waves to another of said plurality of zones along said one of said plurality of scan lines, wherein the step of scanning includes the step of receiving the reflected energy waves, such that an image of said object is generated according to said reflected ultrasonic waves.

28. The method as in claim 27 wherein each of said steps is performed dynamically, such that said ultrasonic waves are focused during transmission and reception in real-time.

29. The method as defined in claim 27 further comprising the step of performing mix line sequencing, such that after the reflected ultrasonic waves from one of said plurality of focal point on one of said lines is received, the ultrasonic waves are transmitted to one of said plurality of focal points on another of said lines.

30. An apparatus for generating an image on an object having discontinuities comprising:

transmitter means for transmitting energy waves for imaging at a plurality of depths within an object, wherein the transmitter means includes means for optimizing the bandwidth of said energy waves for each of said plurality of depths, means for optimizing the frequency for each of said plurality of depths, and means for maintaining the aperture, wherein the transmitter means transmits the energy waves into the object along a plurality of scan lines, such that each of the plurality of depths has a single frequency and bandwidth to localize the energy waves at each of the plurality of depths while maintaining the aperture, wherein the reflected energy waves from depths outside any one of the plurality of depths are reduced in strength when transmitting energy waves to said one of the plurality of depths to avoid interference with the reflected energy waves from said one of said plurality of depths, such that all of the reflected energy waves along one of said plurality of scan lines from one of said plurality of depths is not received before transmitting energy waves to another of said plurality of depths along said one of said plurality of scan lines, such that said waves are localized to said plurality of depths; and receiving means for receiving reflected energy waves corresponding to reflections of energy waves from the discontinuities within a given depth, wherein an image of said object is generated according to said reflected energy waves received by said receiving means.

31. The apparatus as defined in claim 30 wherein said transmitting means focuses said waves dynamically, such that the image of said object is generated in real-time.

32. The apparatus as defined in claim 30 wherein said bandwidth is optimized for each of said plurality of depths by varying burst length with depth, such that the burst length is reduced for depths nearer into said object.

33. An apparatus for generating an ultrasonic image on an object having discontinuities comprising:

transmitter means for transmitting ultrasonic waves for imaging at a plurality of depths within an object, wherein the transmitter means includes means for dynamically focusing said ultrasonic waves at said plurality of depths, such that the ultrasonic waves are localized for each of said plurality of depths, wherein the means for dynamically focusing includes means for optimizing the bandwidth of said ultrasonic waves, wherein the burst length is varied, such that the burst length of said ultrasonic waves is reduced for depths nearer into said object in order to optimize the transmit frequency for each of said plurality of depths, and wherein the means for dynamically focusing includes means for optimizing the frequency for each of said plurality of depths and means for maintaining the aperture, wherein the transmitter means transmits the ultrasonic waves into the object along a plurality of scan lines, such that each of the plurality of depths has a single frequency and bandwidth to localize the ultrasonic waves at each of the plurality of depths while maintaining the aperture, wherein the reflected ultrasonic waves from zones outside any one of the plurality of depths are reduced in strength when transmitting ultrasonic waves to said one of the plurality of depths to avoid interference with reflected ultrasonic waves from said one of the plurality of depths, such that all of the reflected ultrasonic waves along one of said plurality of scan lines from one of said plurality of depths is not received before transmitting ultrasonic waves to another of said plurality of depths along said one of said plurality of scan lines; and receiving means for receiving reflected ultrasonic waves corresponding to reflections of ultrasonic waves from the discontinuities within a given depth, wherein said receiving means performs focusing of said reflected ultrasonic waves, such that said receiving means is focused to receive ultrasonic waves from the depth at which said transmitting means is focusing the transmission of ultrasonic waves, wherein an image of said object is generated in real-time according to said reflected ultrasonic waves received by said receiving means.

34. The apparatus as defined in claim 33 wherein said receiving means is dynamically focused for receiving said ultrasonic waves.

35. The apparatus as defined in claim 33 wherein said transmitter means optimizes the intensity of said waves for said plurality of zones by increasing the intensity of waves for the deeper of said plurality of zones.

36. A system for producing images of a portion of a body utilizing wave energy which is reflected from reflectors within said body, said portion being comprised of a plurality of zones, said system comprising:

source means for transmitting a plurality of concentrated beam profiles of wave energy into said body, such that each of said plurality of beam profiles is focused at one of said zones within said body, and wherein said plurality of beam profiles are transmitted in a specific temporal order. such that at least one of said beam profiles is transmitted to one of said plurality of zones, said one zone being non-adjacent to the zone of the previously transmitted beam profile, wherein the source means includes means for optimizing the transmit frequency of the wave energy for each of said plurality of zones, such that the wave energy is localized at said plurality of focal points within said body, means for optimizing the bandwidth of said wave energy for each of said plurality of zones, such that the wave energy is localized at said plurality of focal points within said body, and means for maintaining the aperture size of said wave energy, such that the size of said plurality of zones remains small during transmission, wherein the source means concentrates wave energy into the object along a plurality of scan lines, such that each of the plurality of depths has a single frequency and bandwidth to localize the wave energy at each of the plurality of depths while maintaining the aperture, wherein the reflected wave energy from zones outside any one of the plurality of depths are reduced in strength when concentrating wave energy in said one of the plurality of depths to avoid interference with the reflected wave energy from said one of the plurality of depths, such that all of the reflected wave energy along one of said plurality of scan lines from one of said plurality of depths is not received before transmitting wave energy to another of said plurality of depths along said one of said plurality of scan lines, and, receiving means for receiving the reflected wave energy from said reflectors in said body, wherein said source means transmits the next of said plurality of beam profiles after said receiving means receives the reflected wave energy from the maximum depth of the beam profile preceding said next of said beam profiles.

37. The system as defined in claim 36 wherein said plurality of beam profiles is focused in real-time.

38. The system as in claim 36 wherein the frequency of said next of said beam profiles is lower than the frequency of said beam profile preceding said next of said beam profiles.

39. A method for imaging an object in a body using energy waves, wherein said waves are transmitted from a source into said body according to a set of time delays and transmit parameters and are reflected from discontinuities within said body, said method comprising the steps of:

selecting a plurality of zones, wherein said plurality of zones have a plurality of focal points, wherein each of said plurality of focal points is associated with one of said plurality of zones, such that the energy can be localized at said plurality of focal points within said body;

determining the time delays between transmits necessary to ensure that energy waves subsequently transmitted to one of said focal points do not interfere with the reception of reflected energy waves from the remaining of said plurality of focal points; and focusing continuously said energy waves in a plane during transmission and reception into a body at said plurality of focal points, including focusing said energy which is out of said plane, such that the size of each of said plurality of zones may be reduced producing an improved focus, wherein the step of continuously focusing energy waves includes the steps of optimizing the transmit frequency of the energy waves for each of said plurality of zones, such that the energy is localized at said plurality of focal points within said body;

optimizing the bandwidth of the energy waves for each of said plurality of zones, such that the energy is localized at said plurality of focal points within said body;

maintaining the aperture size of said waves, such that the size of said plurality of zones remains small during transmission, such that the energy waves for each of the plurality of zones has a single frequency and bandwidth to localize the energy waves in each of the plurality of zones, wherein the reflected energy waves from zones outside any one of the plurality of zones are reduced in strength when transmitting ultrasonic waves to said one of the plurality of zones, wherein the energy waves are transmitted into the body along a plurality of scan lines and reflected energy waves are produced, such that all of the reflected energy waves along one of said plurality of scan lines from one of said plurality of zones is not received before transmitting energy waves to another of said plurality of zones along said one of said plurality of scan lines, such that an image of said object is generated according to said reflected ultrasonic waves.

* * * * *